United States Patent [19]

Kay et al.

[11] 4,293,221

[45] Oct. 6, 1981

[54] MULTIDIMENSIONAL SLIT-SCAN FLOW SYSTEM

[75] Inventors: David B. Kay, Rochester; Leon L. Wheeless, Jr., Webster; James L. Cambier, Rome, all of N.Y.

[73] Assignee: Research Corporation, New York, N.Y.

[21] Appl. No.: 30,880

[22] Filed: Apr. 17, 1979

[51] Int. Cl.³ ............................................. G01J 21/64
[52] U.S. Cl. .................................. 356/318; 250/461 B
[58] Field of Search ..................... 356/318; 250/461 B

[56] References Cited

U.S. PATENT DOCUMENTS

| | | | |
|---|---|---|---|
| Re. 29,141 | 2/1977 | Hogg ................................ | 356/39 X |
| 2,656,508 | 10/1953 | Coulter ................................ | 324/71 |
| 3,327,117 | 6/1967 | Kamentsky . | |
| 3,327,119 | 6/1967 | Kamentsky . | |
| 3,470,373 | 9/1969 | Brewer et al. . | |
| 3,497,690 | 2/1970 | Wheeless, Jr. et al. .......... | 356/51 X |
| 3,578,978 | 5/1971 | Laurent ................................ | 250/221 |
| 3,657,537 | 4/1972 | Wheeless, Jr. et al. ............. | 356/39 |
| 3,699,336 | 10/1972 | Ehrlich et al. ..................... | 356/39 X |
| 3,705,771 | 12/1972 | Friedman et al. ..................... | 356/39 |
| 3,710,933 | 1/1973 | Fulwyler et al. ................. | 356/39 X |
| 3,770,349 | 11/1973 | Legorreta-Sanchez .............. | 356/73 |
| 3,785,735 | 1/1974 | Friedman et al. ..................... | 356/39 |
| 3,788,744 | 1/1974 | Friedman et al. ..................... | 356/39 |
| 3,883,247 | 5/1975 | Adams ................................ | 356/39 |
| 3,910,702 | 10/1975 | Corll ................................ | 356/72 |
| 3,918,812 | 11/1975 | Holm ................................ | 356/72 |
| 3,960,449 | 6/1976 | Carleton et al. ................. | 250/574 X |
| 4,031,399 | 6/1977 | Klein et al. ....................... | 250/461 B |

OTHER PUBLICATIONS

"Photomicrography of Deep Fields", Simon, Rev. of Sci. Inst., vol. 36, No. 11, pp. 1654-1655 (Nov. 1965).
J. L. Cambier, D. B. Kay and L. L. Wheeless, Jr., "A Multi-Dimensional Slit-Scan Flow System", J. Histochem. Cytochem., vol. 27, No. 1, pp. 321-324 (1979).
D. B. Kay, J. L. Cambier and L. L. Wheeless, Jr., "Imaging in Flow", J. Histochem. Cytochem., vol. 27, No. 1, pp. 329-334 (1979).
J. L. Cambier and L. L. Wheeless, Jr., "Predicated Performance of Single-versus Multiple-Slit Flow Systems", J. Histochem. Cytochem., vol. 27, No. 1, pp. 325-328 (1979).
L. L. Wheeless, Jr., J. L. Cambier, M. A. Cambier, D. B. Kay, L. L. Wightman and S. F. Patten, Jr., "False Alarms in a Slit-Scan Flow System: Causes and Occurrence Rates Implications and Potential Solutions", J. Histochem. Cytochem., vol. 27, No. 1, pp. 596-599 (1979).
J. E. Gill, L. L. Wheeless, Jr., C. Hanna Madden, R. J. Marisa and P. K. Horan, "A Comparison of Acridine Orange and Feulgen Cytochemistry of Human Tumor Cell Nuclei", Cancer Research 38 (Jul., 1978).
L. L. Wheeless, Jr., D. B. Kay, M. A. Cambier, J. L. Cambier and S. F. Patten, Jr., "Imaging Systems for Correlation of False Alarms in Flow", J. Histochem. Cytochem., vol. 25, No. 7, pp. 864-869 (1977).
D. B. Kay, J. L. Cambier and L. L. Wheeless, Jr., "Imaging System for Correlating Fluorescence Cell Measurements in Flow", Proceedings of the Society of Photo-Optical Instrumentation Engineers, San Diego, Calif., Clever Optics, vol. 126, pp. 132-138 (Aug. 25-26, 1977).
D. B. Kay and L. L. Wheeless, Jr., "Laser Stroboscopic Photography Technique for Cell Orientation Studies in Flow", J. Histochem. Cytochem., vol. 24, No. 1, pp. 265-268 (1976).
J. A. Hardy and L. L. Wheeless, Jr., "Application of Fraunhofer Diffraction Theory to Feature-Specific Detector Design", J. Histochem. Cytochem., vol. 25, No. 7, pp. 857-863 (1977).
L. L. Wheeless, Jr., S. F. Patten, Jr. and M. A. Onderdonk, "Quantitative Comparision of Slide and Suspension Technique for Acridine Orange Staining of Human Cells", Acta Cytol., vol. 18, No. 1, pp. 8-12 (1974).
L. L. Wheeless, Jr. and M. A. Onderdonk, "Preparation of Clinical Gynecologic Specimens for Automated Analysis", J. Histochem. Cytochem., vol. 22, No. 7, pp. 522-525 (1974).
M. A. Cambier, L. L. Wheeless, Jr. and S. F. Patten, Jr., "A New Post-Staining Fixation Technique for Acridine Orange", Acta Cytol., vol. 21, No. 3, pp. 477-480 (1977).
J. S. Mead, P. K. Horan and L. L. Wheeless, Jr., "Syringing as a Method of Cell Dispersal/I. Effect on Intermediate and Superficial Squamous Cells", *Acta Cytol.*, vol. 22, No. 2, pp. 86–90, (1978).

L. L. Wheeless, Jr. and S. F. Patten, Jr., "Slit–Scan Cytofluorometry", *Acta Cytol.*, vol. 17, No. 4, pp. 333-339 (1973).

J. L. Cambier and L. L. Wheeless, Jr., "Stochastic Models for Multistage Cell Classification Systems", *IEEE Transactions on Biomedical Engineering*, vol. BME-25, No. 4 (Jul., 1978).

J. L. Cambier and L. L. Wheeless, Jr., "Binucleate Cell Recognition in Automated Gynecologic Cytopathology", *Acta Cytol.*, vol. 22, No. 6, pp. 523–529 (1978).

L. L. Wheeless, Jr. and S. F. Patten, Jr., "Slit–Scan Cytofluorometry: Basis for an Automated Cytopathology Prescreening System", *Acta Cytol.*, vol. 17, No. 5, pp. 391–394 (1973).

L. L. Wheeless, Jr., S. F. Patten, Jr. and M. A. Cambier, "Slit–Scan Cytofluorometry: Data Base for Automated Cytopathology", *Acta Cytol.*, vol. 19, No. 5, pp. 460–464 (1975).

M. A. Cambier, W. J. Christy, L. L. Wheeless, Jr. and I. N. Frank, "Slit-Scan Cytofluorometry Basis for Automated Prescreening of Urinary Tract Cytology", *J. Histochem. Cytochem.*, vol. 24, No. 1, pp. 305-307 (1976).

L. L. Wheeless, Jr., J. A. Hardy and N. Balasubramanian, "Slit–Scan Flow System for Automated Cytopathology", *Acta Cytol.*, vol. 19, No. 1, pp. 45–52 (1975).

J. L. Cambier and L. L. Wheeless, Jr., "The Binucleate Cell: Implications for Automated Cytopathology", *Acta Cytol.*, vol. 19, No. 3, pp. 281–285 (1975).

D. B. Kay and L. L. Wheeless, Jr., "Experimental Findings on Gynecologic Cell Orientation and Dynamics for Three Flow Nozzle Geometries", *J. Histochem. Cytochem.*, vol. 25, No. 7, pp. 870–874 (1977).

*Primary Examiner*—Vincent P. McGraw
*Attorney, Agent, or Firm*—Kerkam, Stowell, Kondracki & Clarke

[57] ABSTRACT

Flow systems for photometric analysis of particles, such as biological cells, particularly for obtaining multidmensional slit-scan type contours, as well as other images. In one broad approach, fluorochrome-stained cells in suspension flow through a focused slit of laser excitation light defining a planar excitation region in the X-Y plane. As each fluorochrome-stained cell flows through the excitation region, fluorescence emissions are generated at the intersection of the excitation region and the cell. To generate a slit-scan type contour along the Z axis, fluorescence emissions are monitored as the cell flows through the excitation region and a plurality of substantially planar parallel cross-sections of the cell along the Z axis are excited to fluorescence. To generate slit-scan type contrours along the cellular X and Y axes, various optical system embodiments define various combinations of cellular linear portions within the Z axis cross-section. The fluorescence or other emissions from these cellular linear portions are then combined by integrating to generate the desired contours. In another broad approach described, a three-dimensional volume of a cell in flow is illuminated with exciting radiation which is not a narrow beam. Three optical systems view a central point in the flow system. The optical systems are slit-imaging and have three respective axes orthogonal to each other and symmetrically located about the stream such that the axis of flow forms equal angles with each optical axis. A photomultiplier tube for each optical system detects the imaged cell fluorescence.

63 Claims, 21 Drawing Figures

MULTIDIMENSIONAL SLIT-SCAN FLOW SYSTEM

Support for this invention was received through National Cancer Institute Contract No. NO1-CB-33862.

BACKGROUND OF THE INVENTION

The present invention relates generally to an automated cytopathology screening instrument and, more particularly, to a flow cytofluorometer or photometer for simultaneously obtaining multidimensional slit-scan type fluorescence or other photometric contours of particles, particularly biological cells, in flow.

A number of approaches have been developed directed to the problem of automating the process of analyzing cells from biological specimens. One particular, but not limiting, purpose is automated prescreening for gynecologic cancer and its precursors. A successful system must achieve a desired sensitivity to the few abnormal cells (have a low false negative rate), and at the same time maintain acceptable false positive rates. That is, the system must not generate an excessive number of false alarms which lead to the necessity of subsequent manual examination. These functional considerations should preferably be satisfied in a cellular screening system which has a high cell throughput, and which minimizes the amount of complex computation in the analysis required. This basically translates to a question of system resolution.

At one end of the resolution scale are high-resolution systems, for example utilizing a sub-micron scanning spot, wherein a full two-dimensional image of each cell is acquired and processed by a computer. This can involve relatively long data processing and computation times, and consequent low throughput. At the other end of the resolution scale are low-resolution systems wherein excitation and measuring apertures are larger than the cell of interest and a gross characteristics of each cell is examined, for example total fluorescence at a particular wavelength or light scatter at a particular angle. These systems permit measurements to be made at rates up to several thousand cells per second, and provide valuable information on specific cellular substances and parameters profiles on large populations of cells. However, they have thus far failed to demonstrate a capability to provide sufficient cellular information for the decisions required for application as a screening instrument.

Particular examples of high-resolution systems are disclosed in the Ehrlich et al U.S. Pat. No. 3,699,336 and in the Holm U.S. Pat. No. 3,918,812.

In low-resolution systems, a number of approaches have been proposed. The Coulter U.S. Pat. No. 2,656,508 describes the Coulter sensing principle which provides an indication of cell size. Of particular interest with respect to the present invention are the low-resolution systems of the following U.S. Patents, which systems generally optically view biological cells from two orientations or simultaneously examine a plurality of optical characteristics: Friedman et al U.S. Pat. Nos. 3,705,771, 3,785,735, and 3,788,744; and Fulwyler et al U.S. Pat. No. 3,710,933. As a particular example, the low-resolution system disclosed in the '933 Fulwyler et al patent includes a flow chamber through which cells in suspension flow sequentially in a stream, and a light beam which intersects the cell stream at right angles. The Fulwyler et al system measures small angle light scatter in one direction, and cellular fluorescence in another. An additional patent, Corll U.S. Pat. No. 3,910,702 describes a low-resolution system which is of interest with respect to certain particular aspects of the present invention in that an optical detector views particles along an axis of flow.

One particularly promising medium-resolution measurement technique suitable for use in the field of automated cytology is a slit-scan technique invented by L. L. Wheeless, Jr., and S. F. Patten, Jr. This technique is described in the Wheeless, Jr., et al U.S. Pat. No. 3,657,537 and in the literature reference: L. L. Wheeless, Jr., and S. F. Patten, Jr., "Slit-Scan Cytofluorometry", *Acta Cytol.*, vol. 17, no. 4, pp. 333–339 (1973). These references provide the details of a static cell slit-scan cytofluorometer.

The slit-scan technique provides a more complete set of cellular parameters than is available with a low-resolution optical system, without producing the large data matrix associated with a high-resolution system. It represents a compromise solution to the problems of throughput and resolution.

In particular, the slit-scan configuration sequentially records the secondary fluorescence of an elongated portion of a cell (generally transversing the width of the cell) at discrete time intervals as that cell moves relative to the slit producing aperture. In a static cell instrument, this may be accomplished by recording the secondary fluorescence through a slit aperture at discrete intervals as that aperture is passed over the cell. This corresponds in a flow system to a recording of secondary fluorescence from a cell as it flows through a thin "wall" of excitation illumination. In both cases the slit aperture, or wall of excitation illumination, ideally is much smaller than the diameter of the cell of interest.

This type of medium-resolution slit-scan provides a graphic fluorescence contour, which in essence is a plot of the averaged fluorescence along the cell. From such contours, the fluorescence from the nuclei of the cells is readily distinguishable from cytoplasmic fluorescence.

The information from such a contour has been shown to be quite useful in prescreening. Specifically, for each cell, such characteristics as nuclear fluorescence, nuclear diameter, cytoplasmic diameter, cytoplasmic fluorescence, and nuclear to cytoplasmic diameter ratio (N/C ratio) may be determined. This technique is becoming increasingly useful since a comparison data base has been developed to enable the recognition of abnormal cells. In addition to the Wheeless and Patten "Slit-Scan Cytofluorometry" article identified above, the following literature references provide additional background information concerning the usefulness of the slit scan technique: L. L. Wheeless, Jr., and S. F. Patten, Jr., "Slit-Scan Cytofluorometry: Basis for an Automated Cytopathology Prescreening System", *Acta Cytol.*, vol, 17, no. 5, pp. 391–394 (1973); L. L. Wheeless, Jr., S. F. Patten, Jr., and M. A. Cambier, "Slit-Scan Cytofluorometry: Data Base for Automated Cytopathology", *Acta Cytol.*, vol. 19, no. 5, pp. 460–464 (1975); and M. A. Cambier, W. J. Christy, L. L. Wheeless, Jr. and I. N. Frank, "Slit-Scan Cytofluorometry Basis for Automated Prescreening of Urinary Tract Cytology", *J. Histochem. and Cytochem.*, vol. 24, no. 1, pp. 305–307 (1976).

In particular, from the Wheeless, Jr., Patten, Jr., and Cambier article entitled "Slit-Scan Cytofluorometry: Data Base for Automated Cytopathology", extensive investigation has shown that nuclear fluorescence from cells stained with Acridine Orange is higher in abnormal cells than in normal cells. The Cambier, Christy, Wheeless, Jr., and Frank article entitled "Slit-Scan Cytofluorometry Basis for Automated Prescreening of Urinary Tract Cytology", demonstrates potential usefulness in a slightly different area.

More recent slit-scan instruments utilize a flow cytofluorometer, details of which are described in: L. L. Wheeless, Jr., A Hardy and N. Balasubramanian, "Slit-Scan Flow System for Automated Cytopathology", *Acta Cytol.*, vol. 19, no. 1, pp. 45-52 (1975). This flow cytofluorometer implements the flow system technique referred to in the Wheeless, Jr. and Patten, Jr. article "Slit-Scan Cytofluorometry", cited above, wherein secondary fluorescence is recorded from a cell as it flows through a thin "wall" of excitation illumination.

In this flow system, relatively transparent, fluorochrome stained cells in suspension ideally flow one-by-one through a focused slit of laser excitation light. Assuming the axis of flow is defined as the Z axis, in essence a planar sheet of excitation light in the X-Y plane is generated defining an excitation region. As the fluorochrome stained cells flow through the excitation region, fluorescence emissions are generated at the intersection of the planar excitation region and the cell. As the cell flows through the excitation region, a plurality of substantially planar parallel cross-sections of the cell along the Z axis are excited to secondary fluorescence. Monitoring the fluorescence emissions generates a slit-scan type contour along the Z axis.

It should be noted that one difference between the static slit-scan cytofluorometer previously described and the flow slit-scan cytofluorometer relates to the difference in the shape of the aperture effective cross-section. In the static cell slit-scan system, the aperture is a true slit which is passed across the fluorescence image of the cell. In the flow system, the sheet of laser light has a Gaussian intensity distribution, in the direction of flow (along the Z axis), and is elliptical in cross-section (in the X-Y plane). This difference is insubstantial in practice, and the expression "slit-scan type contour" as employed herein is intended to refer interchangeably to contours generated by either of these approaches.

One particular problem in evaluating cells by means of a one-dimensional slit-scan type contour along a single axis is that false alarms may occur as a result of such factors as cell orientation. It has been determined that the majority of false alarms are due to multinucleate cells or overlapping cells oriented such that both nuclei enter the measurement region simultaneously. Such a cell or cells may be completely normal but, in this orientation, exhibit greater nuclear fluorescence than uninuclear cells of the same cell type, and thus be erroneously classified as abnormal. Similarly, the entire cell may be oriented with the plane of the cell parallel to the plane of the slit excitation such that there is substantially no discrimination between cytoplasmic fluorescence and nuclear fluorescence. The problem of binucleate cells is discussed in particular in the literature reference: J. L. Cambier and L. L. Wheeless, Jr., "The Binucleate Cell: Implications for Automated Cytopathology", *Acta Cytol.*, vol. 19, no. 3, pp. 281-285 (1975).

At least four general approaches to solving cell classification problems resulting from particular cellular orientations have been proposed. A first technique is the use of flow nozzles and analysis chambers which tend to produce a desired orientation of the cells. This technique is suggested by the Hogg U.S. Pat. No. Re. 29,141, and in the literature reference: D. Kay and L. L. Wheeless, Jr., "Experimental Findings on Gynecologic Cell Orientation and Dynamics for Three Flow Nozzle Geometries", *J. Histochem. Cytochem.*, vol. 25, no. 7, pp. 870-874 (1977).

A second technique is to provide a second analysis stage which analyzes cells which have recorded a positive event as a result of passage through a first slit-scan type measurement system. The second stage may employ a higher resolution analysis, and may obtain and analyze a two dimensional image. Such techniques are generally described in the following two literature references: L. L. Wheeless, Jr., D. B. Kay, M. A. Cambier, L. Cambier and S. F. Pattern, Jr., "Imaging Systems for Correlation of False Alarms in Flow", *J. Histochem. Cytochem.* vol. 25, no. 7, pp. 864-869 (1977); and D. B. Kay, L. Cambier and L. L. Wheeless, Jr., "Imaging System for Correlating Fluorescence Cell Measurements In FLow", Proceedings of the Society of Photo-Optical Instrumentation Engineers, San Diego, Calif., vol. 126, *Clever Optics,* pp. 132-139 (Aug. 25-26, 1977). (It should be noted that a second stage may still be required with the present invention, but there will be fewer false alarms necessitating second state processing.)

Third, and particularly in the context of a second analysis stage as mentioned immediately above, it has been suggested that a segmented slit technique would be useful. (Wheeless, Kay, Cambier, Cambier, and Patten, "Imaging Systems for Correlation of False Alarms in Flow", above.) This technique produces a plurality of slit-scan type contours, each representing fluorescence across only a portion of the cell, and may be considered a low-resolution form of two-dimensional imagery.

Fourth, it has been recognized that apparatus which would provide one-dimensional slit-scan contours along three orthogonal axes would be quite useful in providing additional information useful in reducing the incidence of false positive indications, particularly those resulting from binucleate or overlapping cells which are oriented such that in a single slit-scan type contour each appears to be an abnormal cell having a high nuclear fluorescence, rather than a binucleate cell or a pair of overlapping cells producing two distinct peaks on the slit-scan contour. The Cambier and Wheeless, Jr. article entitled "The Binucleate Cell: Implications for Automatic Cytopathology", cited above, itself refers to the desirability of a system employing three orthogonal slits. An additional such reference is in the Wheeless, Jr., Hardy, and Balasubramanian article, also cited above, which describes a "Slit-Scan Flow System for Automated Cytopathology". While not prior art with respect to the present invention, a more recent analysis of false alarms may be found in L. L. Wheeless, Jr., J. L. Cambier, M. A. Cambier, D. B. Kay, L. L. Wightman and S. F. Patten, Jr., "False Alarms in a Slit-Scan Flow Systems: Causes and Occurrence Rates Implications and Potential Solutions", *J. Histochem. Cytochem.*, vol. 27, no. 1, pp. 596-599 (1979).

In particular multi-dimensional slit-scan apparatus such as has been proposed, three successive excitation laser beams are positioned sequentially along the flow axis, oriented in mutually orthogonal planes.

In a multi-dimensional slit-scan flow system, in which three orthogonal projections of cell fluorescence are collected, overlapping cells produce three slit-scan contours. In at least one of these contours the nuclei will in most cases be evidenced by two distinct fluorescence peaks, which can be recognized as such, and the nuclear fluorescence measurement disregarded.

Two particular problems arise with such a sequential multiple slit-scan type instrument. Perhaps the more serious is that cell orientation and/or overlap may change from one measurement station to the next, and the result that the contours are not truly orthogonal, and, depending upon the precise nature of the tumbling between stations, two of the slit-scan contours may actually be along the same axis of the cell. Cell orientation problems in the context of a system employing three orthogonal slit measuring beams are discussed in particular in the reference D. B. Kay and L. L. Wheeless, Jr., "Laser Stroboscopic Photography Technique For Cell Orientation Studies in Flow", *J. Histochem. Cytochem.*, vol. 24, no. 1, pp. 265–268 (1976). Another problem is that a plurality of cell excitations are required, with the result that the cell may become bleached, thus distorting the measurements.

SUMMARY OF THE INVENTION

Accordingly, it is an object of the invention to provide means for improving false alarm rates in prescreening systems for cytology and, more particularly, to achieve the lowest error rates attainable in a single stage, slit-scan flow system.

It is another object of the invention to provide improved apparatus for producing slit-scan type contours along a plurality of cellular axes in a flow cytofluorometer or a flow cytophotometer.

It is another object of the invention to provide apparatus for obtaining slit-scan type photometric contours in general from particles in general, not necessarily limited to cellular or biological particles.

It is another object of the invention to provide a multi-dimensional slit-scan photometer which acquires information from a cell or other particle to generate multiple slit-scan type contours essentially simultaneously, thereby avoiding the inaccuracies resulting from particle orientation changes between measurement station.

It is another object of the invention to provide such apparatus which requires only a single slit of laser excitation illumination, and yet provides multi-dimensional slit-scan contours.

It is yet another object of the invention to provide apparatus for producing relatively high-resolution two-dimensional images of cellular or particle cross-sections, which two-dimensional images either may be read out continuously in real time to provide sequential images, or may be integrated to generate a full two-dimensional image useful in feature extraction.

It is still another object of the invention to provide apparatus useful for obtaining multidimensional slit-scan type photometric contours of radiation in general from cellular or particle interaction with an excitation beam, not limited to measurements of secondary fluorescence. Additional forms of cellular or particle interaction with an excitation beam include light scattering (both small and large angle) and light absorption.

It is still another object of the invention to provide an alternative approach to simultaneously obtaining multidimensional slit-scan type contours, which alternative approach does not require a narrow slit beam of excitation illumination.

The various aspects of the invention which are summarized below are, for convenience, primarily summarized in terms of a flow cytofluorometer for analyzing cellular and biological particles, as this is the application for which the invention was originally developed. However, it will readily be appreciated that the apparatus described is useful for analyzing particles in general, not limited to biological particles.

Briefly stated, and in accordance with one broad aspect of the invention, a flow cytofluorometer for obtaining multidimensional slit-scan type fluorescence contours of biological cells includes a conventional means for conveying cells along a flow axis. As in previous slit-scan flow cytofluorometers, there is a means providing a substantially planar beam of electromagnetic radiation for exciting secondary fluorescence in the cells. The beam orientation is such that the flow axis intersects but does not lie within the plane of the beam. As a cell passes through the beam, a plurality of first substantially planar parallel cross-sections of the cell are successively excited to secondary fluorescence. In one particular embodiment, the plane of the beam is perpendicular to the flow axis. Further, there is provided a means for measuring secondary fluorescence from the first cellular cross-sections as the cell passes through the beam so as to generate a conventional slit-scan type contour along a first axis perpendicular to the first cellular cross-sections.

In accordance with the invention, linear portions of a first plurality are defined by the intersections of each of a plurality of second substantially planar parallel cross-sections of the cell with each of the first cellular cross-sections, the second cellular cross-sections being parallel to the flow axis. A means is provided for measuring secondary fluorescence from each of the first plurality of substantially linear portions of the cell as the cell passes through the beam, and for generating first integrations for individual second cellular cross-sections of the measured secondary fluorescences of all the linear portions therein. The resultant first integrations collectively represent a slit-scan type contour along a second axis perpendicular to the second cellular cross-sections.

In further accordance with the invention, where it is desired to provide a third slit-scan type contour, linear portions of a second plurality are defined by intersections of each of a plurality of third substantially planar parallel cellular cross-sections with each of the first cellular cross-sections. The third cellular cross-sections are parallel to the flow axis and not parallel to the second cellular cross-sections. A means is provided for measuring secondary fluorescence from each of a second plurality of substantially linear portions of the cell as the cell passes through the beam, and for generating second integrations for each individual third cellular cross-section of the measured secondary fluorescences of all the linear portions therein. The resultant second integrations collectively represent a slit-scan type contour along a third cellular axis perpendicular to the third cross-sections.

Preferably, the plane of the beam of electromagnetic radiation is perpendicular to the flow axis, and the second and third planar portions are perpendicular to each other. in this case, a Cartesian coordinate system may be defined wherein the first or flow axis is termed the Z axis, the second axis perpendicular to the second cellular cross-sections may be termed the cellular X axis, and the third axis perpendicular to the third cellular cross-sections may be termed the cellular Y axis.

More particularly, in specific embodiments implementing one particular approach of the invention, which may be termed a side imaging approach, the means for measuring secondary fluorescence from each of a first plurality of substantially linear portions and for generating first integrations collectively representing a slit-scan type contour along a second cellular axis comprises a first linear array of photodetector elements responsive to secondary fluorescence. A first imaging means images the linear portions of the first plurality onto the first linear array as each of the first cellular cross-sections passes through the beam and is excited to fluorescence. The first imaging means produces end-on imaging of individual linear portions of the first plurality which lie in each of the first cellular cross-sections. That is, each first cellular cross-section is viewed along its plane such that each linear portion appears as an elemental area. The cytofluorometer additionally includes means for integrating with respect to time the secondary fluorescences of the linear portions imaged on each photodetector element. Preferably, this means for integrating is included within the photodetector elements. Accordingly, after the cell has passed completely through the beam, the individual integrations collectively represent a slit-scan type contour along the second cellular axis.

Similarly, the means for measuring secondary fluorescence by means of a second plurality of substantially linear portions and for generating second integrations collectively representing a slit-scan type contour along a third cellular axis comprises a second linear array of photodetector elements response to secondary fluorescence. A second imaging means images the linear portions of the second plurality onto the second linear array as each of the first cellular cross-sections passes through the beam and is excited to fluorescence. The second imaging means produces end-on imaging of individual linear portions of the second plurality which lie in each of the first cellular cross-sections passes through the beam and is excited into fluorescence. The second imaging means produces end-on imaging of individual linear portions of the second plurality which lie in each of the first cellular cross-sections. There is also provided a means for integrating also preferably is included within the photodetector elements themselves, by providing time integrating photodetector elements.

In another particular approach of the invention, which may be termed an on-axis imaging approach, the means for measuring secondary fluorescence from each of a first plurality of substantially linear portions and for generating first integrations collectively representing a slit-scan type contour along a second cellular axis comprises a first linear array of parallel elongated photodetector elements responsive to secondary fluorescence. In these particular embodiments, a first imaging means images the linear portions of the first plurality onto the first linear array of elongated photodetector elements as each of the first cellular cross-sections passes through the beam and is excited to fluorescence, but in this case the first imaging means produces said imaging (perpendicular to the illuminated first cellular cross-section) of individual linear portions of the first plurality which lie in each of the first cellular cross-sections onto corresponding photodetector elements. Each first cellular cross-section thus is viewed in a direction perpendicular to its plane such that each linear portion appears as a strip. The cytofluorometer includes means for integrating with respect to time the secondary fluorescences of the linear portions imaged on each photodetector element.

The means for measuring secondary fluorescence from each of a second plurality of substantially linear portions and for generating second integrations collectively representing a slit-scan type contour along a third cellular axis similarly comprises a second linear array of parallel elongated photodetector elements responsive to secondary fluorescence, and second means for imaging the linear portions of the second plurality onto the second linear array of elongated photodetector elements as each of the first cellular cross-sections passes through the beam and is excited to fluorescence. The second imaging means also produces side imaging (perpendicular to the illuminated first cellular cross-sections) of individual linear portions of the second plurality which lie in each of the first cellular cross-sections onto corresponding photodetector elements. Lastly, there is provided means for integrating with respect to time the secondary fluorescences of the linear portions imaged on each photodetector element of said second linear array.

In the side imaging approach of the invention briefly described above, generally the optical systems for the X and Y axis slit-scans image along a pair of axes perpendicular to each other and each perpendicular to the flow axis, assuming the plane of the excitation illumination is perpendicular to the flow axis. In the event the plane of the excitation illumination is not perpendicular to the flow axis, then the optical axes of the imaging means would be within the plane of the excitation illumination.

In the on-axis imaging approach of the invention briefly described above, generally a shared optical system for the X and Y axis slit-scans images along an axis coincident with the flow axis, assuming the plane of excitation illumination is perpendicular to the flow axis. In the event the plane of the excitation illumination is not perpendicular to the flow axis, then preferably the optical axis would still be perpendicular to the plane of the excitation illumination.

It will be appreciated that various hybrid approaches are also possible, whereby X and Y axis optical systems would view the excitation region along optical axis intermediate to an axis lying in the excitation plane and an axis perpendicular to the excitation plane. Compared to the on-axis imaging approach, this would require shorter individual elongated elements in the array of photodetector elements, possibly simplify the optical system by not requiring coincidence between the optical axis and the flow axis, but would sacrifice part of the potentially superior resolution of the on-axis imaging approach by requiring a greater depth of focus.

In another form of on-axis imaging, a single two-dimensional array detector is employed. This array detector may be read out in various ways to provide X and Y axis slit-scan contours, sequential two-dimensional images with high resolution of individual cellular cross-sections, or a full cellular two-dimensional image at high resolution useful for feature extraction.

In accordance with another broad aspect of the invention, a narrow beam or slit of exciting radiation is not employed. Rather a three-dimensional volume of the cell is illuminated with exciting radiation. Three optical systems view a central point in the flow stream, which central point is within the excited volume. The optical systems have three respective orthogonal axis each of which is oblique to the flow axis. Preferably the optical axes are symmetrically located about the flow stream such that the axis of flow forms equal angles with each optical axis. A slit field stop is employed in the image plane of each optical system, and each of the three slits is oriented to be parallel to each of the three planes respectively of an X-Y-Z coordinate system. In this particular coordinate system, none of the slit-scan axes corresponds with the flow axis, as was possible in the previously-described embodiments. Behind each slit field stop, a photomultiplier tube detects the imaged cell fluorescence, and each slit thus provides a scanned signal spatially orthogonal to the others.

This particular system is less complex to implement than the previously-described systems, but has the disadvantage of lower slit-scan resolution than the side view or on-axis view-systems which implement the first broad aspect of the invention discussed above. This is due to the increased depth of focus required to image across the stream obliquely. Additionally, increased cell bleaching can also occur since the excited region is large compared to the region excited by a slit-type beam.

In accordance with still another aspect of the invention, the slit-focussed laser excitation embodiments are potentially useful as flow cytometers in general for obtaining multidimensional photometric contours. In this case, the photodetectors respond to radiation resulting from interaction of cellular material with the excitation laser beam. This radiation may be the result of light scattering (small or large angle) or light transmission through portions of the cell (decreased by absorption by cellular bodies), as well as the result of fluorescence as previously described.

It should be noted that aspects of the present invention have been disclosed in literature published less than one year prior to the filing date hereof. Specifically: J. L. Cambier, D. B. Kay and L. L. Wheeless, Jr., "A Multi-Dimensional Slit-Scan Flow System", *J. Histochem. Cytochem.*, vol. 27, no. 1, pp. 321-324 (1979); D. B. Kay, J. L. Cambier and L. L. Wheeless, Jr., "Imaging In Flow", *J. Histochem. Cytochem.*, vol. 27, no. 1, pp. 329-334 (1979); J. L. Cambier and L. L. Wheeless, Jr., "Predicted Performance of Single- versus Multiple-Slit Flow Systems", *J. Histochem. Cytochem.*, vol. 27, no. 1, pp., 325-328 (1979); and L. L. Wheeless, Jr., J. L. Cambier, M. A. Cambier, D. B. Kay, L. L. Wightman and S. F. Patten, Jr., "False Alarms in a Slit-Scan Flow System: Causes and Occurrence Rates Implications and Potential Solutions", *J. Histochem. Cytochem.*, vol. 27, no. 1, pp. 596-599 (1979). The entire disclosure of each of these four literature references is hereby expressly incorporated by reference herein. This enumeration of specific publications should not, however, be taken as implying that other acts of publication less than one year prior to the filing date hereof have not occurred, and no such representation is made or intended herein.

It is anticipated that the X-Y-Z slit-scan systems of the invention will effect a significant improvement in false alarm rates in prescreening systems for gynecologic cytology. In reducing the false alarm rate from the previous 3% to well below 1%, the invention will in all likelihood provide the lowest single cell error rates attainable in a single stage slit-scan flow system.

For a more detailed discussion from a statistical viewpoint of the probability that a binucleate cell will be recognized as such by a multidimensional slit-scan flow system, reference may be had to the above-cited Cambier and Wheeless, Jr. article entitled "Predicted Performance of Single- versus Multiple-Slit Flow Systems." This article in part concludes that a contour processing algorithm able to recognize binucleate cells with observed nuclear spacing greater than 0.8 nuclear diameters, for example, would detect 40% of binucleate cells in a single-slit flow system, and 70% of those passing through a three-slit system. A far greater proportion of doublet or overlapping cells would be correctly recognized in a multidimensional system, since their true nuclear spacing is greater than that of binucleate cells.

In the particular processing apparatus described hereinbelow, each of three separate slit-scan contours along respective mutually orthogonal cellular axes are examined for a double peak indicative of a binucleate cell. If any one contour is double-peaked, then nuclear fluorescence data from the particular cell involved is rejected as an indicator of abnormality, thereby avoiding what likely would be a "false positive" event.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DESCRIPTION OF THE PREFERRED EMBODIMENTS

Preliminarily, it should be noted that while the particular apparatus described in detail herein is for analyzing cellular or biological particles, this is for the purposes of illustration only, and the invention may as well be employed for analyzing particles of other types.

Figure 1:
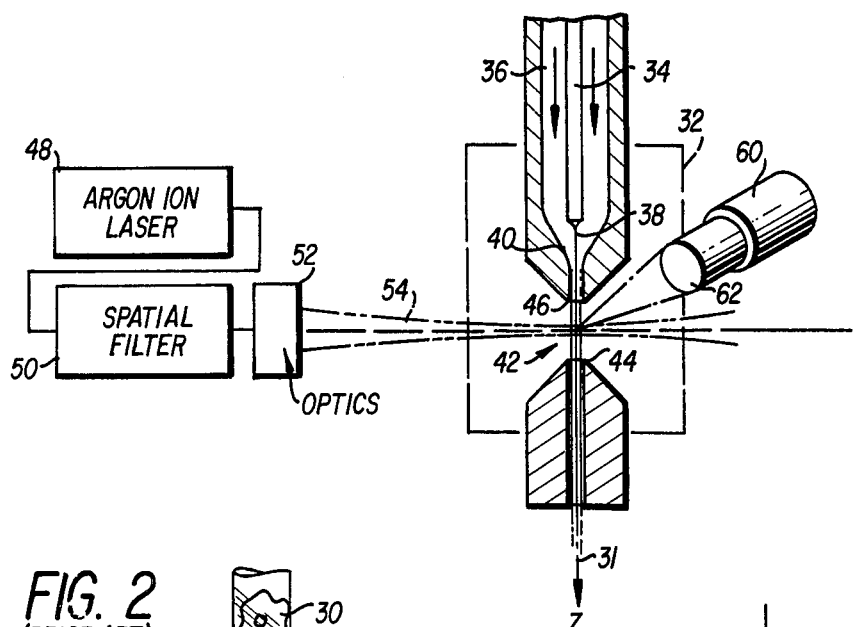
FIG. 1 is a highly schematic perspective view of a prior art slit-scan flow cytofluorometer.
Figure 2:
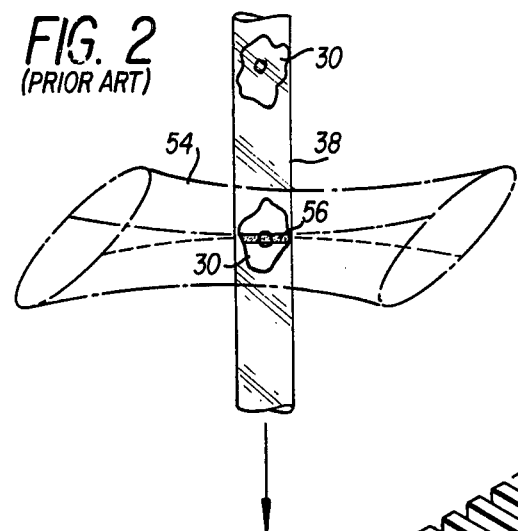
FIG. 2 is a greatly enlarged view of the sampling region of the prior art slit-scan flow cytofluorometer of FIG. 1 showing the elliptical cross-section of the excitation laser beam exciting a substantially planar cross-section of a cell in flow.

Referring now to FIGS. 1 and 2, there is shown in diagrammatic form a prior art slit-scan flow cytofluorometer, such as is described in the references: L. L. Wheeless, Jr., J. A. Hardy and N. Balasubramanian, "Slit-Scan Flow System for Automated Cytopathology", *Acta Cytol.*, vol. 19, no. 1, pp. 45–52 (1975); and D. B. Kay, J. L. Cambier and L. L. Wheeless, "Imaging System for Correlating Fluorescence Cell Measurements in Flow", *SPIE*, vol., 126 *Clever Optics,* pp. 132–139 (1977), the entire disclosures of which are hereby incorporated by reference. It will be appreciated that such a one-dimensional flow cytofluorometer comprises the basic framework around which multi-dimensional flow cytoflyorometers in accordance with the present invention are constructed.

For conveying cells 30 along a flow axis 31 (Z axis), a flow chamber 32 employing a sheath flow geometry is employed. Fluorochrome (Adridine Orange) stained cells 30 in suspension enter the chamber 32 via an axial specimen tube 34 and are enveloped in a coaxial sheath of water 36. A stream 38 of cell 30 in suspension exits the specimen tube 34 and is constricted in a flow nozzle 40. At this point, the cell stream 38 has a diameter which is approximately that of the individual cells 30.

The cell stream 38 flows across a gap region 42, and exits the chamber 32 via a capillary tube 44. The gap region 42 is typically 200–350 micrometers from the exit 46 of the flow nozzle 40 to the entrance of the capillary tube 44, with a typical flow rate of 10 to 50 cm/sec. The flow is laminar in the capillary tubes 34 and 44. Preferably, the flow nozzle 40 is elliptical, and produces a cell stream 38 having an elongated cross-section. For further information concerning such sheath flow nozzles, the reference D. B. Kay and L. L. Wheeless, Jr., "Experimental Findings on Gynecologic Cell Orientation and Dynamics for Three Flow Nozzle Geometries", *J. Histochem. Cytochem.,* vol. 25, no. 7, pp. 870–874 (1977) may be consulted.

To generate a substantially planar beam of electromagnetic radiation for exciting secondary fluorescence in the cells 30 as they cross the gap region 42, a 0.1 to 0.5 watt, 488 nanometer argon-ion laser 48 is brought to a line focus via a spatial filter 50 and a suitable optical system 52. The actual elliptical shape of the laser beam 54 cross-section is best seen in FIG. 2, wherein it may also be seen that a substantially planar cross-section 56 of the cell 30 is excited to secondary fluorescence. It will be appreciated that, due to the actual elliptical shape of the laser beam 54 cross-section with Gaussian intensity distribution, the cell illuminated cross-section 56 is not precisely planar, but for purposes of the invention, may be considered to be substantially planar. The beam 54 enters the flow chamber 32 preferably via an aplanatic window (not shown), minimizing optical aberrations. The highest practical resolution for the laser line focus, and thus the fluorescence contour, is fixed by the required depth of focus. The required depth of focus is based on the dimensions of the largest cells 30 present, or the width of the stream 38, whichever is greater. Cells in gynecologic specimens can be up to fifty micrometers in diameter. As a particular example, for the Gaussian beam waist (line focus) to remain within ±6% across the cell stream 38, the line focus may be designed to be 6.62 micrometers at $1/e^2$ pts or 3.9 micrometers full width at half maximum (FWHM).

Although not strictly necessary in the single dimension slit-scan flow cytofluorometer of FIG. 1 wherein the laser line focus establishes the effective slit-scan aperture, the general requirements of an imaging optical system which is required by the present invention for imaging the fluorescence regions of the cells 30 will now for convenience be described with reference to FIGS. 1 and 3. Due to the cylindrical shape of the cell stream 38, significant aberrations would occur in an optical system which employed fluid-to-air and air-to-glass interfaces. One approach to minimizing such aberrations would be a custom design optical system.

An alternative method of circumventing the need for such custom lens design is to eliminate the optical interfaces by employing a water immersion microscope objective lens protruding into the fluid environment. For example, in FIG. 3, the coaxial cell stream 38 flows across the gap region 42, within a fluid filled chamber 32'. A water immersion microscope objective lens 58 is shown projecting into the chamber 32'.

For measuring secondary fluorescence from successive cellular cross-sections 56 as the cells 30 pass through the beam 54 so as to generate a slit scan-type contour along the flow axis (Z axis), a photomultiplier tube 60 is provided, with a suitable lens system 62. The lens system 62 may include a suitable filter for transmitting only fluorescent radiation of a selected wavelength, and discriminating against the wavelength of the laser 48.

Figure 4:
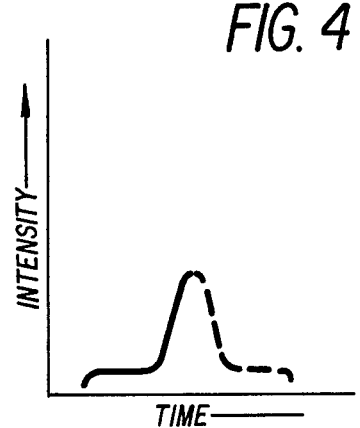
FIG. 4 is a graph showing a typical slit-scan type contour such as would be produced along the flow axis (Z-axis) of the cytofluorometer shown schematically in FIGS. 1 and 2.
Figure 3:
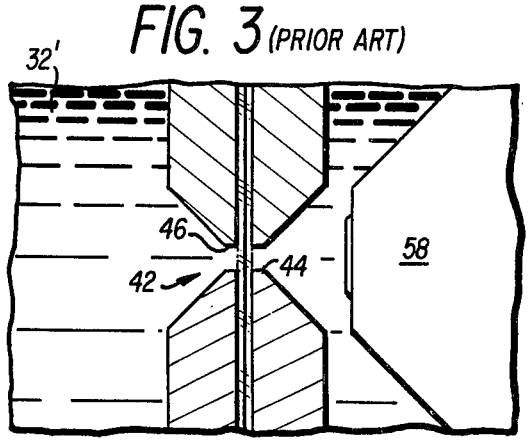
FIG. 3 is an enlarged view of a flow nozzle and a portion of an optical system, including a water immersion microscope objective lens, in a flow cytofluorometer such as is depicted in FIGS. 1 and 2.

FIG. 4 illustrates a typical one-dimensional slit-scan type contour such as is generated at the output of the photomultiplier tube 60 in the cytofluorometer of FIGS. 1-3 as a single cell 30 passes through the excitation laser beam 54, and successive cross-sections, such as the cross-section 56 of the cell 30 are excited to secondary fluorescence. The hump of the FIG. 4 curve represents the nuclear fluorescence, while the shoulders represent the cytoplasmic fluorescence. As is discussed in greater detail in the literature and patents mentioned in the "Background of the Invention," useful information concerning the cells 30, such as nuclear fluorescence and nuclear to cytoplasmic (N/C) ratio, may be derived from such a contour.

The prior art slit-scan flow system of FIGS. 1-3 generates a slit-scan type contour along only a single axis. In the illustrated case where the plane of the laser excitation region is perpendicular to the flow axis, the slit-scan type contour as represented by FIG. 4 may be termed a slit-scan contour along the Z-axis, flow axis, or first cellular axis.

Figure 5:
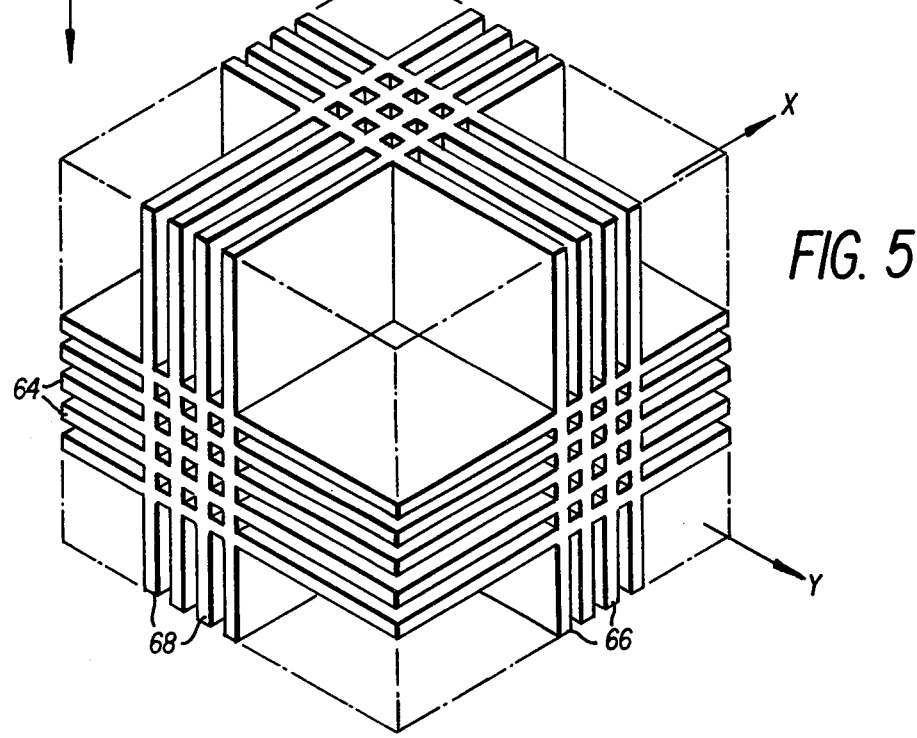
FIG. 5 is a highly schematic isometric illustration of the manner in which a cell is effectively partitioned into planar cross-sections by multi-dimensional flow cytofluorometers embodying the present invention.

Referring now to FIG. 5, the manner in which a cell is effectively partitioned into substantially planar cellular cross-sections by multi-dimensional flow cytofluorometers according to the present invention is depicted. For convenience, an X-Y-Z Cartesian coordinate system is assumed, and the Z-axis and the flow axis coincide. It will be appreciated that the relative dimensions chosen for purposes of illustration are completely arbitrary, and that the thickness of the individual planar sections reflects the resolution of the system. It will further be appreciated that, due to such factors as the elliptical laser beam cross-section, the sections are not precisely planar, but may be so considered for practical purposes.

In FIG. 5, a plurality of first substantially planar parallel cellular cross-sections 64 represent those which are optically defined by prior art single axis slit-scan flow cytofluorometers such as is depicted in FIGS. 1-3. The fluorescence intensity as represented at any single point on the curve of FIG. 4 corresponds to the total fluorescence of all of the cellular material within one of the first cellular cross-sections 64. Each of the first cellular cross-sections 64 is defined at any given instant by the relative positioning of the particular cell 30 and the laser excitation beam 54. It will be appreciated that, as the cell 30 flows across the gap region 42 and through the laser beam 54, an infinite number of overlapping first cellular cross-sections 64 are generated. It will be further appreciated that in accordance with conventional analysis techniques, the output of the photomultiplier tube 60 may be sampled at discrete times.

Additionally depicted in FIG. 5 are a plurality of second substantially planar parallel cellular cross-sections 66 which are parallel to the Z or flow axis, and preferably are perpendicular to the first cellular cross-sections 64. These second cross-sections 66 are contiguous along a second cellular axis (X axis) perpendicular to the second cross-sections 66. Lastly, in FIG. 5 are depicted a plurality of third substantially planar parallel cellular cross-sections 68, which also are parallel to the flow axis, and preferably are orthogonal to the first cellular cross-section 64 and the second cellular cross-sections 66. These third cross-sections 68 are contiguous along a third cellular axis (Y axis) perpendicular to the third cross-sections 68.

Figure 6:
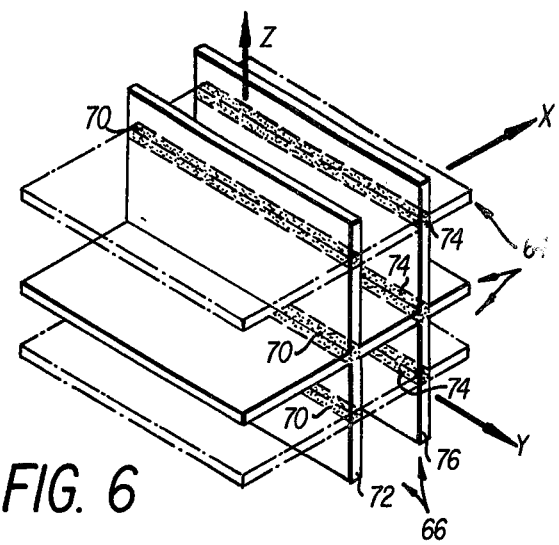
FIG. 6 is a portion of the FIG. 5 representation showing in particular how the fluorescences of each of a plurality of individual second cellular cross-sections are generated by integrating the secondary fluorescences of all the linear portions therein.

With reference now to FIG. 6, which is a portion of the FIG. 5 representation, the manner in which the fluorescences of each of the plurality of individual second cellular cross-sections 66 are optically defined in accordance with an important concept of the invention is illustrated. From FIG. 6, it will be seen that at each intersection of one of the cellular cross-sections 64 of the first plurality with one of the cellular cross-sections 66 of the second plurality, a substantially linear portion of the cell is defined. In FIG. 6, representative substantially linear portions 70 are depicted lying within a particular one 72 of the second parallel cellular cross-sections 66, and substantially linear portions 74 are depicted as lying within a particular one 76 of the second cellular cross-sections 66. It will be appreciated that the actual cellular portions represented by the linear portions 70 and 74 may not be precisely linear, and may not have the precise boundaries such as are illustrated for purposes of convenient example in the illustrations. The particular shape of the linear portions depends upon the precise intensity distribution of the laser beam 54 which effectively defines the first cellular cross-section 64, as well as of the effective aperture characteristics of the means, hereinafter described, which defines the second cellular cross-section 66.

Considering the particular second cellular cross-section 72 of FIG. 6, it will be appreciated that the total secondary fluorescence of the cross-section 72 is equal to the sum of the fluorescences of the individual linear portions, such as the exemplary linear portions 70, within the cellular cross-section 72. In accordance with the invention, there is provided a means for measuring secondary fluorescences from the linear portions, such as the exemplary linear portions 70, as the cell passes through the beam and successive first cross-sections 64 are excited to fluorescence. This means additionally generates first integrations for each individual second cross-section 66, such as the exemplary cross-section 72, of the measured secondary fluorescences of all the linear portions 70 therein. Each resultant first integration represents a single point on a slit-scan type contour along a cellular axis, for example, the X-axis perpendicular to the second cross-sections 66, and the resultant first integrations collectively represent a slit-scan type contour along the second or X-axis.

Figure 7:
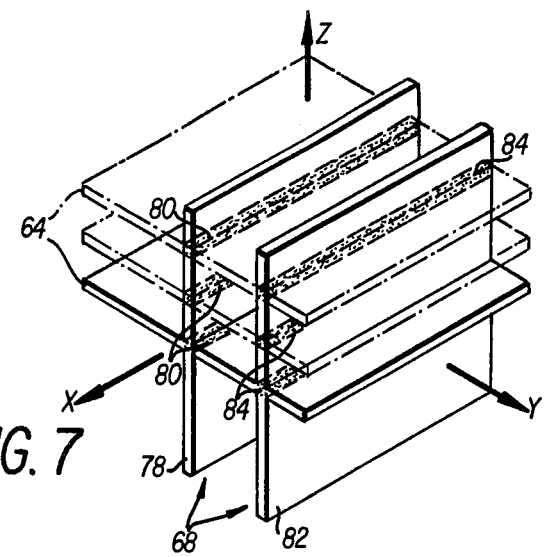
FIG. 7 is another portion of the FIG. 5 representation showing in particular how the fluorescences of each of a plurality of individual third cellular cross-sections are generated by integrating the secondary fluorescences of all the linear portions therein.

FIG. 7 similarly illustrates the manner in which the third cellular cross-sections 68 are defined. A particular one 78 of the third cellular cross-sections 68 has exemplary linear portions 80 lying therein, while another particular one 82 of the third cellular cross-sections 68 has exemplary linear portions 84 lying therein. In accordance with the invention, means are provided for measuring and for generating second integrations for each of the individual third cross-sections 68, such as a particular cross-section 78, of the measured secondary fluorescences of all the linear portions, such as the linear portions 80, therein. Each resultant second integration represents a point on a slit-scan type contour along the third cellular axis (Y-axis) perpendicular to the third cellular cross-sections 68, and the resultant second integrations collectively represent a slit scan-type contour along the cellular third or Y-axis.

Figure 8:
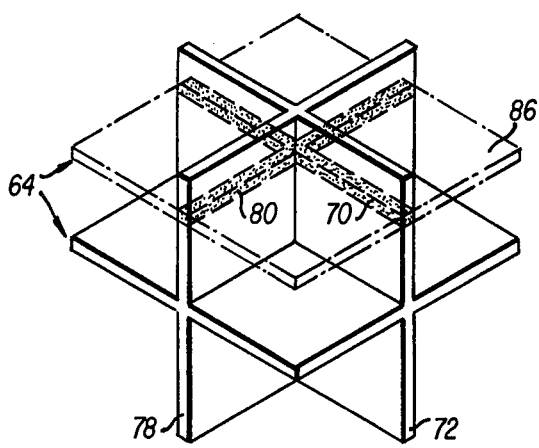
FIG. 8 is a combination of the representations of FIGS. 6 and 7 showing in particular how a linear portion of one of the plurality of second cellular cross-sections and a linear portion of one of the plurality of third cellular cross-sections are derived from an exemplary single one of the first cellular cross-sections.

FIG. 8 depicts how the fluorescence of one of the linear portions, such as the linear portion 70 of the particular one 72 of the second parallel cross-sections 66, and the fluorescence of the linear portion 80 of the particular one 78 of the third cellular cross-sections 68 are measured simultaneously with the measuring of the secondary fluorescence from an exemplary one 86 of the first cellular cross-sections 64 which collectively represent a conventional Z-axis slit-scan contour.

Figure 9:
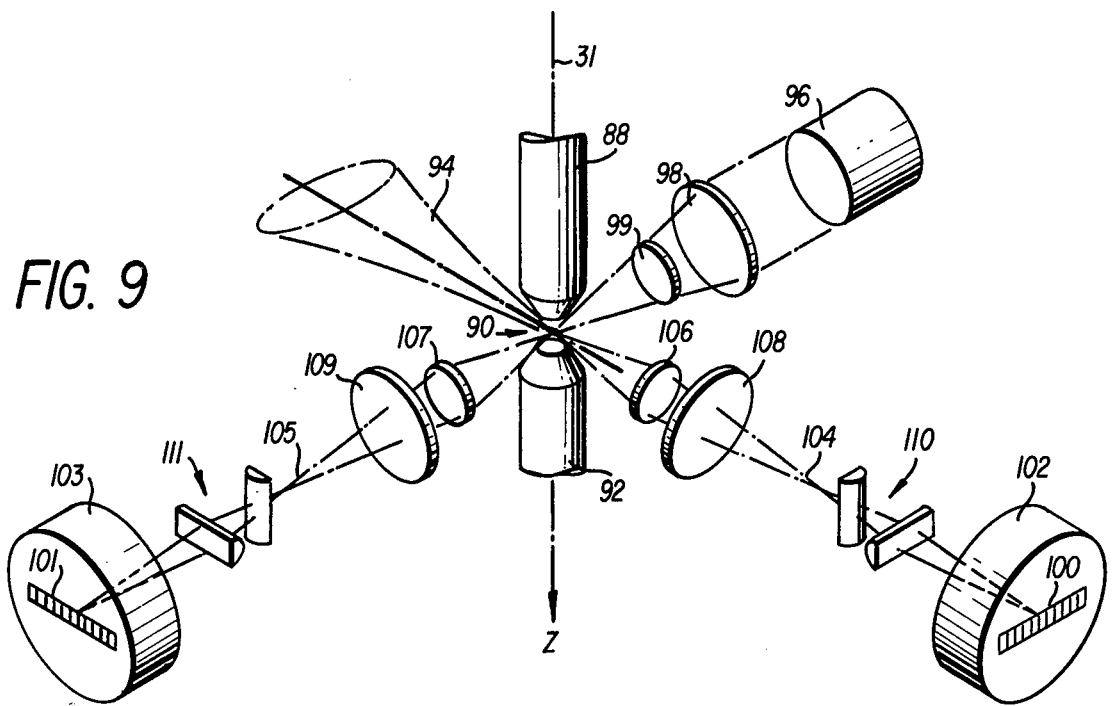
FIG. 9 is a highly schematic representation, similar to that of FIG. 1, but illustrating a side imaging embodiment of the present invention capable of producing slit-scan type contours in three orthogonal orientations; orientations.

Referring now to FIG. 9, there is shown a highly schematic representation of a cytofluorometer embodying a side imaging approach according to the invention, which cytofluorometer is constructed around a prior art single axis slit scan flow cytofluorometer such as is illustrated in FIGS. 1, 2 and 3. In FIG. 9, a sheath flow nozzle 88 flows cells through a gap region 90 into an exit capillary assembly 92. A slit-focussed laser beam 94 is focussed to a four micrometer thick slab of 488 nanometer excitation illumination in the gap region 90. To collect the fluorescence to generate the Z-axis slit-scan contour, a photomultiplier tube 96 views the gap region 90 through a 540 nanometer optical filter 98, which transmits cellular fluorescence, and a water immersion microscope objective lens 99 (magnification X20, numerical aperture 0.40).

As thus far described, the FIG. 9 cytofluorometer is identical to the one-dimensional slit-scan flow systems of the prior art. The signal from the photmultiplier tube 96 is a slip-scan contour Z(z'), and results from cellular fluorescence emissions integrated in the plane of excitation. The contour may be expressed as:

$$Z(z') = \int\int g(x,y,z')dxdy$$

$$g(x,y,z) = \int (C\,x,y,z-\xi)I(\xi)d\xi$$

where:
C(x,y,z) is the distribution of fluorescence emitters in the cell, and
I(z) is the laser beam irradiance profile along the direction of flow.

since the cell is flowing along the Z axis, with velocity V, z'=Vt and Z(z') is generated as a function of time, t. The Z(z') signal is a convolution of the excitation beam profile with the fluorescence distribution of the cell, assuming no saturation effects, and is limited in resolution by the FWHM of I(z) (four micrometers).

In accordance with an aspect of the invention, the slit-scan contour along the X-axis of each cell 30 is collected by a first semi-conductor linear array photodetector 100 which integrates fluorescence from the intersection region of the cell 30 and excitation beam 94 during the time the cell 30 is passing through the excitation region. The resultant information, stored in the array 100 in the form of an electric charge, represents the sampled X-axis contour, and results from integrating the three-dimensional fluorescence intensity distribution along the cellular Y and Z dimensions (with reference to the cellular reference axes of FIG. 5).

The cellular Y-axis slit-scan contour is collected in a similar manner by a second semiconductor linear array photodetector 101. The Y array 101 integrates in the X and Z cullular dimension, and samples along the Y cellular dimension. (Again with reference to the cellular axes of FIG. 5).

After the cell 30 has passed through the excitation region, the X and Y arrays 100 and 101 are read out by array control electronics. Each of the individual detectors of the array 100, after the cell has passed through the excitation region, has stored therewithin the total fluorescence in a single one of the second cellular cross-sections 66. Similarly, each element of the array 101 has stored therewithin the total fluorescence of a single one of the third cellular cross-sections 68, the total fluorescence resulting from integration.

More particularly, the linear arrays 100 and 101 are one hundred twenty-eight element charge coupled photodiode (CCPD) linear arrays coupled to eighteen millimeter microchannel plate intensifiers 102 and 103, which each provide a photon gain of approximately 10,000 in image irradiance before detection by the arrays 100 and 101. Suitable CCPD linear arrays are Type No. CCPD 256, manufactured by Reticon Corporation, Sunnyvale, California. Suitable image intensifiers 102 and 103 are Type No. F-4111, manufactured by ITT Corporation, Fort Wayne, Ind. The Type No. CCPD 256 arrays actually each have two hundred fifty-six elements, with only half of each array used in this particular application.

The two linear arrays 100 and 101 have respective optical imaging means on respective first and second optical axes 104 and 105 oriented at right angles to each other and to the flow axis (Z axis). More particularly, the first and second optical imaging means along the optical axes 104 and 105 comprise respective water immersion microscope objective lenses 106 and 107 (magnification X10, numerical aperture 0.25 stopped down to 0.12), respective wavelength bandpass filters 108 and 109 which transmit the secondary fluorescence, and finally anamorphic optics 110 and 111 (crossed cylinder lenses) which focus the images, with different magnifications in the tagential and sagittal planes (relative to the flow stream) onto the intensifiers 102 and 103. The resultant depth of focus is approximately fifty four micrometers, sufficient to image the entire thickness of a cell when viewed edge-on.

The imaging means on the respective optical axis 104 and 105 thus produce end-on imaging of the linear cellular portions onto individual photodetector elements of the arrays 100 and 101 (through the image intensifiers 102 and 103). For example, the linear portions 70 of FIG. 6 are successively imaged onto one of the elements of the array 100, while the FIG. 6 linear portions 74 are successively imaged onto another one of the elements of the array 100. Similarly, the FIG. 7 linear portions 80 and linear portions 84 are respectively successively imaged onto elements of the photodetector array 101. Each photodetector element then effectively integrates the secondary fluorescences of all the linear portions imaged thereon.

Following integration, reading out the arrays 100 and 101 provides the X and Y slit-scan contours, which may respectively be expressed as:

$$X(x) = \int\int\int g(x,y,z)h(x-\chi)dydzd\chi$$

and $$Y(z) = \int\int\int g(x,y,z)h(y-\psi)dxdzd\psi,$$

where: h(x) is the effective spread function for the combination of the lens system, image intensifier, and array apertures.

In the flow cytofluorometer of FIG. 9, optical resolution is 4.0 micrometers for the Z contour, and 3.5 micrometers for the X and Y contours. Cell velocity is 0.5 m/sec, and contours are digitized at a one MHz rate to provide a spatial sampling interval of 0.5 micrometer. Cell throughput rate is approximately one-hundred cells per second.

With the particular arrangement of FIG. 9, as the linear portions of each cell are imaged on the discrete photodetector elements of the arrays 100 and 101, corresponding discrete and contiguous second cellular cross-sections 66 (FIGS. 5 and 6) and third cellular cross-sections 68 (FIGS. 5 and 7) are optically defined. This is in contrast to the first cellular cross-sections 64 (FIGS. 5, 6 and 7) which continuously merge as the Z-axis slit-scan contour is generated, although discrete first cellular cross-sections 64 may in effect be defined by sampling at discrete points in time, with subsequent analog-to-digital conversion if desired.

Figure 10:
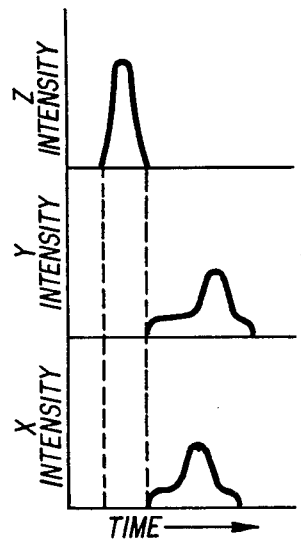
FIG. 10 is a graph similar to FIG. 4, but depicting three separate slit-scan type contours generated by the flow cytofluorometer of FIG. 9.

The operation of the flow cytofluorometer of FIG. 9 is represented by the waveforms of FIG. 10. As a cell passes through the laser excitation region, the output of the photomultiplier tube 96 is the Z axis slit-scan contour Z(z'), which is generated in real time. After cell passage, the image intensifiers 102 and 103 are gated off, and the X and Y arrays 100 and 101 are allowed to integrate the residual phosphorescence from the intensifier output phosphor for approximately one microsecond. (The P-20 phosphor used in the intensifiers has a decay time of 0.5 to 1.0 microsecond, depending on input light level.) After this delay time, the X and Y arrays 100 and 101 are clocked out, generating the analog contours designated "Y intensity" and "X intensity" in FIG. 10.

From FIG. 10, it will be seen that the Z axis slit-scan contour for the particular example chosen does not yield much information, possibly because the plane of the cell was substantially parallel to the plane of the excitation region. However, the X and Y slit-scan contours yield more meaningful information. From at least one of these the desired cellular characteristics may be determined. Similarly, had the cell been binucleate, it is probable that at least one of the three slit-scan contours would be double-humped to reflect the two nuclui, allowing the analysis apparatus to recognize the cell as binucleate.

Before leaving FIG. 9, it should be noted that in the particular flow cytofluorometer of FIG. 9, the required integration to generate the X and Y slit-scan contours is conveniently achieved by the use of time-integrating photodetector arrays. However, it will be appreciated that non-integrating photodetector elements may be employed, and the outputs thereof electrically integrated through suitable circuitry.

Referring now to FIGS. 11–14, there are illustrated four additional embodiments which share the common characteristic of generally producing on-axis imaging of each first cellular cross-section 64 (FIGS. 5, 6 and 7) as it is excited to fluorescence, and resultant side imaging of the individual linear portions of the cell. In these embodiments, the optical systems for the X and Y slit-scan contours are generally coincident with the flow axis, and thus the optical axis is perpendicular to the beam 94 of electromagnetic excitation radiation. This is being accomplished by an optical system which views the excitation region from the underside, employing an apertured objective lens and/or apertured mirror through which cells pass after imaging. Although the particular systems depicted image from the bottom, it will be appreciated that on-axis imaging from the top alternatively may be employed, in which case cells pass through the lens, and/or mirror aperture prior to imaging.

The on-axis imaging approach has the potential of better resolution in that the lens system may have a much narrower depth of focus, the depth of focus required being essentially the thickness of the substantially planar excitation laser beam. All other areas of the cell are out of focus, but this presents no problem because they are not excited to fluorescence anyway. This is similar to the prior art technique known as optically sectioning a cell wherein only sections of the cell which are of interest are in focus, and all other sections are out of focus.

More particularly, the depth of focus $\delta$ of an optical lens system may be expressed as:

$$\delta = \frac{\lambda \sqrt{n^2 - (N.A.)^2}}{(N.A.)^2}$$

where:
$\lambda$ is the wavelength of light imaged,
n is the refractive index of the immersion fluid in the space between the cell and objective lens, and
N.A. is the numerical aperture of the lens.

In the side imaging system of FIG. 9, the depth of focus $\delta$ is required to be at least as great as the diameter of a cell, and preferably, due to cell positional uncertainty, as great as the flow stream diameter. However, in the on-axis imaging systems of FIGS. 11–14, only a thin cross-section of each cell (corresponding to the thickness of the excitation laser beam 94) need be imaged in focus. The significance of this may be appreciated from the following expression for resolution (given in terms of its inverse, $\Delta$, which is the dimension of the smallest detail which can be resolved. A smaller $\Delta$ indicates higher resolution). The expression is applicable for a well-corrected microscope objective lens operating diffraction limited:

$$\Delta = 0.61\lambda/N.A.$$

Thus, resolution is related to depth of focus $\delta$ by the value of the numerical aperture. Requiring a narrower depth of focus permits a higher resolution.

Figure 11:
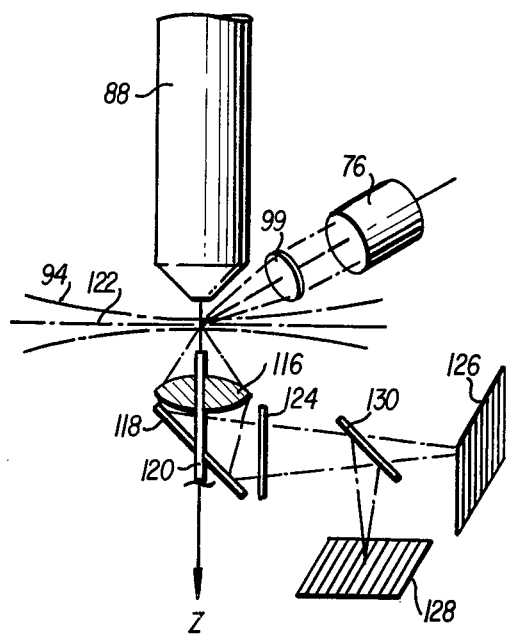
FIG. 11 is a schematic representation of an on-axis imaging embodiment of the invention wherein the axis of the optical system for generating the slit-scan contours along the X and Y cellular axes may be conicident with the flow axis.

In the embodiments of FIGS. 11–14, the flow nozzle 88 may remain essentially unchanged from FIGS. 1 and 9. However, the exit capillary of the flow chamber is replaced by a lens and/or mirror, both containing an aperture along the optical axis through which the cells exit the flow chamber. Specifically, FIG. 11 illustrates a lens 116 and mirror 118, together with an exit capillary 120. It will be seen that the lens 116 is thus effective to provide the desired side imaging of the individual linear portions of the cell, while the mirror 118 physically folds the optical axis.

The line focused laser beam 94 along an axis 122 intersects the Z or flow axis at the working distance of the lens 116. Since the line focused laser excitation along the Z axis is four micrometers in thickness, cells fluoresce only in the region of best focus for the lens 116, and no out of focus objects are excited to fluorescence. Thus the prior art technique referred to above of optically sectioning a cell is enhanced by these embodiments of the invention. A good choice for the lens 116 is a water-immersion objective lens having a numerical aperture (N.A.) of 0.40, a resolution of approximately one micrometer, and a depth of focus of 4.5 micrometers.

The overall optical system comprising the lens 116 and mirror 118 images each of the first cellular cross-sections through a filter 124 onto first and second linear arrays 126 and 128 of parallel elongated photodetector elements responsive to cellular secondary fluorescence as transmitted by the filter 124. Preferably, the arrays 126 and 128 are optically oriented such that the two sets of cellular linear portions defined by being imaged on the elements of the two arrays 126 and 128 are perpendicular. A beam splitter 130 is employed to split the light for imaging on the two arrays 126 and 128. While the two arrays 126 and 128 may be said to have respective first and second imaging means, it will be appreciated that in the illustrated embodiments the first and second imaging means share many common elements, including the lens 116 and 124. It is only after the beam splitter 130 that separate first and second imaging means for the arrays 126 and 128 become apparent.

In operation, as cells flow through the slit excitation region, sections of the cell having a thickness of approximately four micrometers are imaged sequentially on the arrays 126 and 128, each array element responding to all of the light emitted by one of the linear portions of the excited first cellular cross-section at one time. In other words, each array element in effect is a slit aperture having the entire width of each cellular first cross-section imaged thereon. After the cell passes completely through the laser excitation beam 94, readout of the array 126 provides the X-axis slit-scan signal, and readout of the array 128 provides the Y-axis slit-scan signal. Compared to the arrays 100 and 101 in the FIG. 9 embodiment, the resultant information stored in the FIG. 11 arrays 126 and 128 is substantially identical. However, readout of the elongated array elements takes slightly longer due to a longer RC time constant.

Arrays 126 and 128 having less elongated elements could be used by employing anamorphic optics to compress the images in the direction of integration, although there is a practical limit to the compression achievable.

In FIG. 11, the photomultiplier tube 76 and lens 99 remain unchanged from the embodiment of FIG. 9, and generate a prior art type slit-scan type contour along the Z or flow axis.

Figure 12:
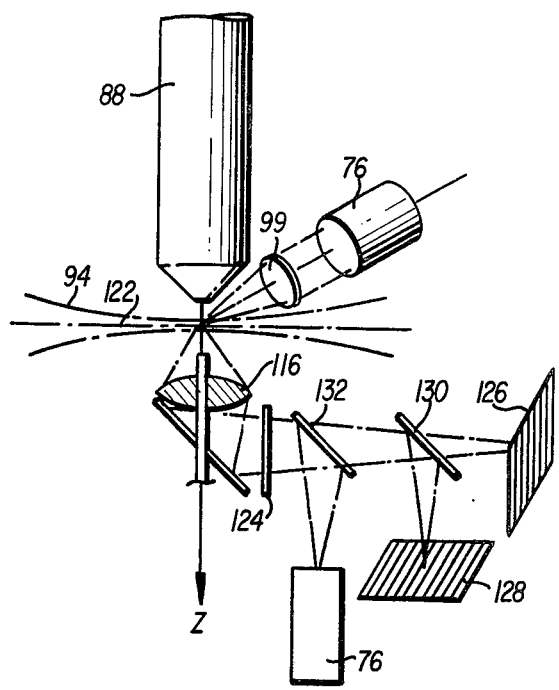
FIG. 12 depicts an embodiment of the invention, similar to FIG. 11, but wherein the Z axis slit-scan contour detector shares an optical axis with the X axis and Y axis detectors.

In FIG. 12 a system similar to that of FIG. 11 is depicted, differing in that the Z-axis slit-scan signal is also derived from the imaging optics. This approach serves to reduce cell orientation errors in the Z-axis slit-scan contour. It requires, in addition to the beam splitter 130, an additional beam splitter 132 for the photomultiplier tube 76.

Figure 13:
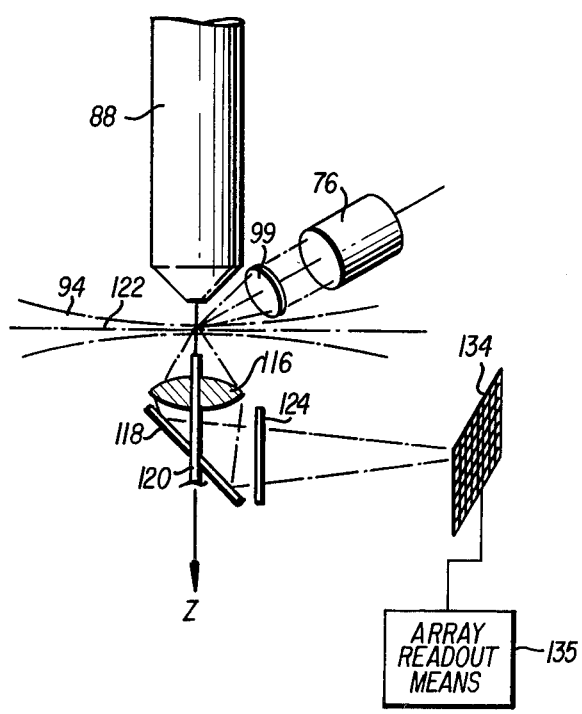
FIG. 13 depicts another embodiment, similar to that of FIG. 11, but wherein a single two-dimensional detector array is employed.

FIG. 13 depicts a variation in the detector configuration. This variation may be employed to obtain X and Y slit-scan contours, but has significant additional utility. In FIG. 13, a single two-dimensional array detector 134 is used in place of the two linear arrays 126 and 128. No beam splitter is employed because there is only the single array 134, and the optical system comprising the lens 126, the mirror 128, and the filter 124 thus serves to image the first cellular cross-sections 64 (FIG. 5) onto the two-dimensional array 134 as each of the cellular cross-sections 64 passes through the beam 94 and is excited to fluorescence. A further element in FIG. 13 is an array readout means 135, compatible with the particular array 134 employed. The readout means 135 performs different functions depending upon the particular information to be obtained.

When X and Y axis slit-scan contours are to be obtained as in the embodiments of FIGS. 11 and 12, a means is included for integrating with respect to time the fluorescence imaged on each element of the array 134. Preferably, this integrating means is included within the array itself by providing time-integrating photo-detector elements in the array 134. The readout means 135 is constructed to read out the array 134 pixel-by-pixel after passage of a cell through the laser excitation beam 94, and then to add (integrate) the pixels in each given row and each given column to produce the X axis and Y axis slit-scan contours. It will be appreciated that the set of integrations by rows represents a slit-scan type contour along one cellular axis, and the set of integrations by columns represents a slit-scan type contour along another cellular axis, perpendicular to the one cellular axis.

While the approach described above is relatively complex and slow (due to readout time for the array 134) compared to previously-described embodiments of the invention for merely obtaining X and Y axis slit-scan type contours, the general approach of employing a single two-dimensional array detector 134 in an on-axis imaging system, with a planar beam of excitation illumination, has other uses.

As one example, where the elements of the array 134 are non-integrating, the array 135 may be continuously read out in real time to provide sequential images as each individual cellular cross-section of the first plurality 64 (FIG. 5) is excited and imaged. In this case, the array 134 may comprise a conventional vidicon, with the output of the readout means 135 being a conventional raster scan video signal.

As another and potentially more useful example, the configuration may be employed to generate a full two-dimensional image or projection of the fluorescent light emitted by a cell. Such an image is quite useful in feature extraction. To accomplish this, a means is included for integrating with respect to the time the fluorescence imaged on each element of the array 134, preferably by providing the time-integrating array elements. After cell passage through the beam 94, the two-dimensional image desired is stored in the array 134, available for readout. This approach provides very good resolution, superior to other two-dimensional imaging techniques, because the optical system depth of focus δ is very narrow compared to cell thickness. Other two-dimensional imaging systems require a depth of focus δ at least as great as cell thickness.

Figure 14:
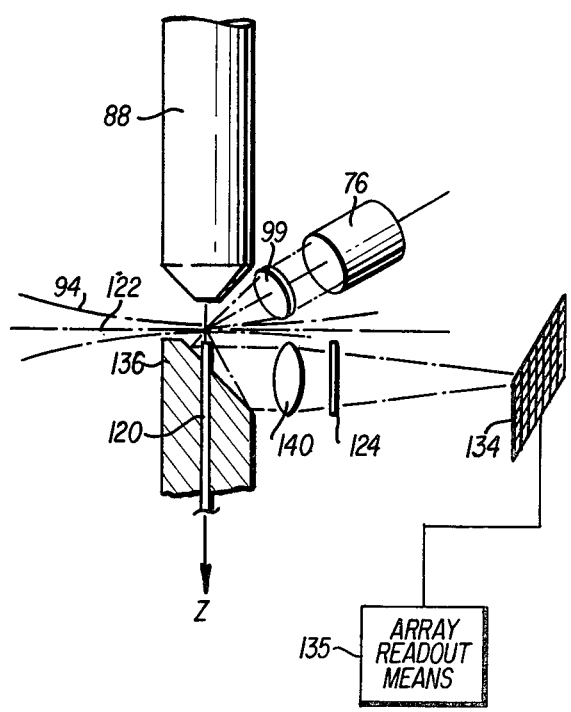
FIG. 14 depicts another embodiment, similar to that of FIG. 13, but employing an alternate optical arrangement.

FIG. 14 illustrates another variation in the optical configuration, wherein the material 136 surrounding the exit capillary 120 is ground and polished at 45° and coated to give a mirror surface. The exit capillary then extends above the 45° surface. A lens 140 with a long working distance is used to one side to gather an axial view of the cell folded by the 45° mirror surface. While it will be immediately appreciated that FIG. 14, with its two-dimensional array detector 134 and readout means 135 is but a minor variation of FIG. 13, and has all of the functional characteristics and advantages discussed immediately above, the array configuration of FIGS. 11 and 12 also may be used in the folded arrangement of FIG. 14.

Although the systems of FIG. 9 and FIGS. 11-14 are described above in terms of a flow system for producing fluorescence contours in three orthogonal orientations, it will be appreciated that the apparatus may more broadly be adapted for photometric analysis in general, including the generation of slit-scan type photometric contours of radiation from cellualar interatiion, such as light scattering and light absorption, with the slit-focussed beam 94. The potential usefulness in particular of light scattered from a line-focussed laser beam is demonstrated by the literature reference J. A. Hardy and L. L. Wheeless, Jr., "Application of Fraunhofer Diffraction Theory to Feature-Specific Detector Design", *J. Histochem. Cytochem.*, vol., 25, no. 7 pp. 857-863 (1977). As this reference indicates, the use of slit-scan light scatter is useful in recognizing the presence of certain boundaries within the cell. Light transmission measurement (decreased by light absorption by cellular features) is similarly potentially useful.

Referring again to FIG. 9, it will be appreciated that the optical filter, such as the filters 112 and 114 may be changed or eliminated so that the photodetectors 100 and 101 respond directly to the wavelength of the laser radiation, rather than to the wavelength of cellular fluorescence. In such event, whether a particular detector and therefore slit-scan orientation is a reflection or scattering contour depends upon the orientation of the optical system with reference to the laser beam. For example, in the FIG. 9 configuration, the output of the array 100 could be read out to produce either a transmission or a small-angle light scatter slit-scan contour along the cellular X axis orientation, and the array 101 read out to provide a large-angle light scatter contour along the cellular Y axis.

The embodiments of FIGS. 11-14 can similarly be modified by changing the wavelength transmitted by the filter 124 (or eliminating the filter 124) so that the detectors 126, 128 and 134 respond directly to the wavelength of the laser radiation.

Figure 15:
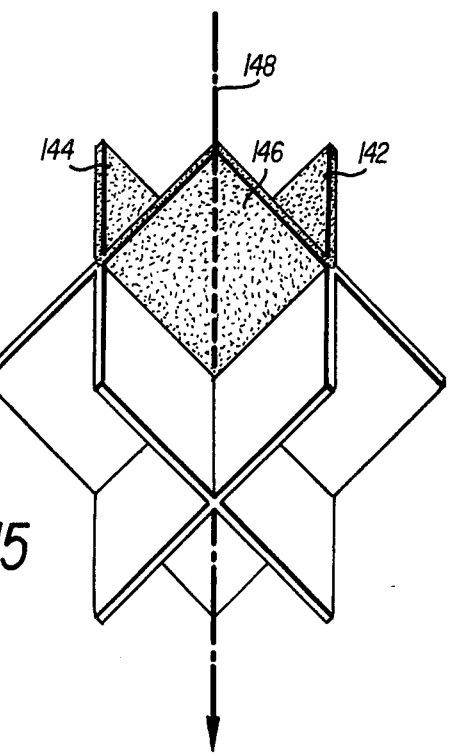
FIG. 15 is a highly schematic representation of an alternative manner in which a cell may be optically partitioned into orthogonal substantially planar cross-sections.

Turning now to the detailed description of another broad approach in accordance with the invention, FIG. 15, which may be contrasted to FIG. 5, is a representation of an alternative manner in which a cell may be effectively partitioned into orthogonal substantially planar cross-sections 142, 144 and 146. In FIG. 15, a flow axis is designated 148 and it will be seen that each of the planar cross-sections 142, 144 and 146 forms an equal angle with the flow axis 148.

Figure 16:
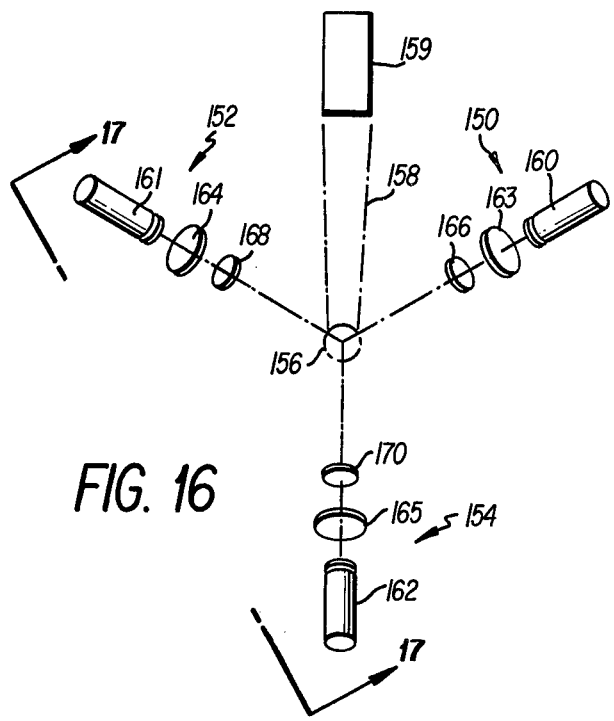
FIG. 16 is a top view of a flow cytofluorometer according to the invention for producing slit-scan type contours in the orientations depicted in FIG. 15.
Figure 17:
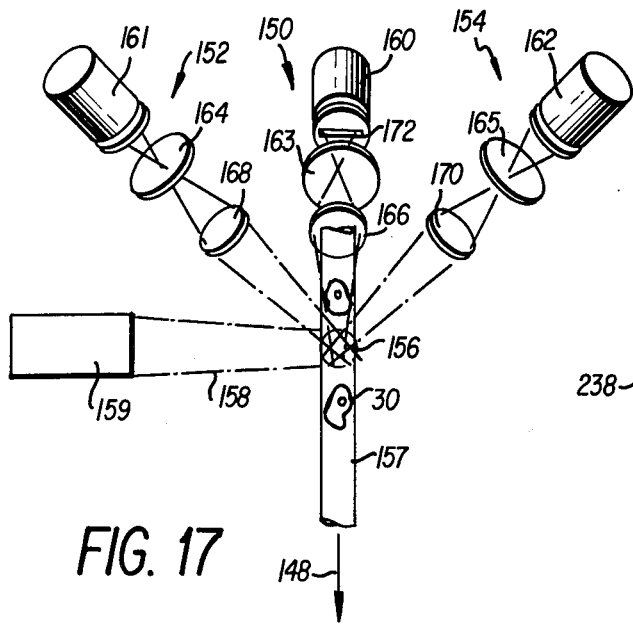
FIG. 17 is an isometric side view of the cytofluorometer of FIG. 16.

To actually implement this approach, a flow cytofluorometer as depicted in FIGS. 16 and 17 may be employed, FIG. 16 being a top view, and FIG. 17 an isometric side view. Three optical systems 150, 152 and 154 comprise respective photomultiplier tubes 160, 161 and 162, respective filters 163, 164 and 165, and respective lenses 166, 168 and 170. A slit field stop, for example, the illustrated slit field stop 172 associated with the photomultiplier tube 160, is employed in the image plane of each of the optical systems 150, 152 and 154, and each of the three slit field stops is oriented to be parallel to a respective one of the three planes of the X-Y-Z coordinate system depicted in FIG. 15. The depth of focus is such that the slit images extend obliquely across the flow stream 158.

In operation, as a cell flows through the region 156, it in effect flows simultaneously through three slit regions. The output of each of the photomultiplier tubes 160, 162 and 164 provides a slit-scan signal spatially orthogonal to the others. It will be appreciated that, in contrast to the embodiments priviously described with reference to FIGS. 1, 9 and 11-12 wherein each cell flows through a thin "wall" of excitation illumination, in the embodiment of FIGS. 16 and 17 the entire cell is illuminated at once (or at least the volume required for all three slit regions), and the slit apertures are exclusively the result of imaging by the optical system.

An advantage of this system is the simpler signal processing required, as no integration is required and all three slit-scan contours are generated in real time. A disadvantage is that lower resolution is achieved because a greater depth of focus is required (increased by $\sqrt{2}$ compared to FIG. 9). Additionally, increased cell bleaching can occur due to cells receiving excitation light over a greater length of the flow stream, possibly affecting the measurement.

Figure 18:
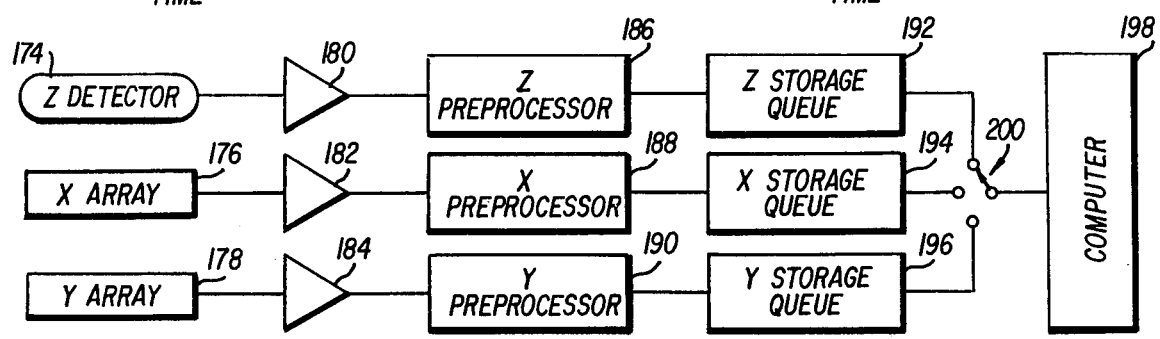
FIG. 18 is an overall electrical block diagram of circuitry suitable for connection to the outputs of any of the embodiments of the invention depicted in FIGS. 9, 11-13, or 16-17.

FIG. 18 is an overall electrical block diagram of circuitry suitable for connection to the outputs of any of the previously-described emobdiments of the invention. While the Z detector 174, and the X and Y arrays 176 and 178 shown at the input of the circuitry of FIG. 18 are suggestive of the embodiments of FIGS. 9 and 11-13 wherein integration is employed to generate is employed to generate the X and Y slit-scan contours, it will be appreciated that a similar scheme may be employed for the embodiment of FIGS. 16 and 17 as well.

In FIG. 18, amplifiers 180, 182 and 184 receive the outputs of the detector 174 or the integrating arrays 176 or 178, depending upon the particular channel. Respective pre-processors 186, 188 and 190 for each channel serve to filter and digitize the cell contours, extract certain preliminary contour features, and perform a number of simple tests which permit rejection of contour data if measurement of nuclear fluorescence is not possible or necessary. If the cell is not rejected, then its three contours are transferred to a set of parallel buffer queues 192, 194 and 196, each one of which may comprise four 128-element Metal Oxide Semiconductor (MOS) shift registers clocked for a one MHz input data rate. Outputs of the queues 192, 194 and 196 are accessed for further processing by a computer 198 via a representative multiplexing switch 200.

Figure 19:
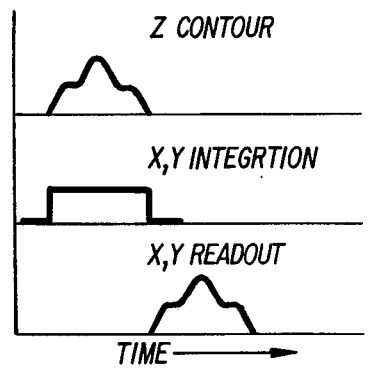
FIG. 19 is a graph of waveforms illustrating a cycle of operation of the system of FIG. 18.

FIG. 19 represents the operation of the processing system of FIG. 186, wherein the Z contour is processed by the pre-processor 18 and stored in the storage queue 192 while the arrays 176 and 178 are integrating the fluorescence information for the X and Y slit-scan contours. Thereafter, the X and Y arrays 176 and 178 are read out, processed through the pre-processors 188 and 190, and the results stored in the queues 194 and 196.

Figure 20:
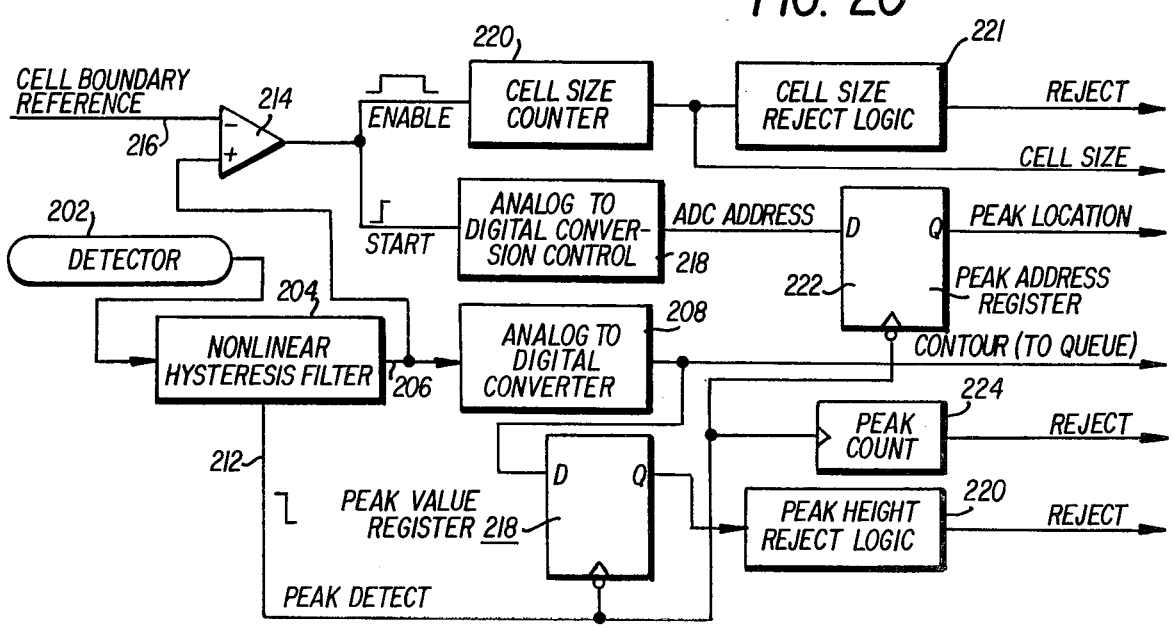
FIG. 20 is an electrical block diagram of one of the pre-processors of the system of FIG. 19.

FIG. 20 is a block diagram of one of the pre-processors 186, 188 or 190 of FIG. 18. An input element is shown as a detector 202, which may be either the Z detector 174 of FIG. 18, or either of X or Y arrays 176 and 178.

The output of the detector 202 is first processed through a non-linear hysteresis filter 204 (described in greater detail below with particular reference to FIG. 21). The non-linear hysteresis filter 204 serves to remove small "dips" or "bumps" in the slit-scan contour. The output 206 of the non-linear hysteresis filter 204 is thus a processed slit-scan contour. More specifically, the filter 204 reproduces only "significant" peaks, where the threshold of significance is set by choice of a reference input $V_T$. By removing minor dips and bumps, subsequent circuitry for recognizing and rejecting double peak contours (from binucleate cells) is simplified.

For basic processing according to the invention, this contour from output 206 is digitized by an analog-to-digital converter 208, and then output along a line 210 to one of the queues, for example the Z storage queue 192 of FIG. 18. The non-linear hysteresis filter 204 also generates a PEAK DETECT output on a line 212 which transitions when the processed slit-scan contour reverses slope at the peak thereof.

To control the analog digital conversion, as well as to control cell size logic, an analog comparator 214 has its non-inverting (+) input connected directly to the output 206 of the non-linear hysteresis filter 204, and compares this output 206 with a cell boundary reference voltage level input on a line 216 which supplies the comparator 214 inverting (—) input. The output of the comparator 214 is connected to a START input of an analog-to-digital conversion control 218, as well as to the ENABLE input of a cell size counter 220 which counts at a fixed rate during the time that the comparator output line is high, thereby providing a representation of cell size. This cell size representation is compared to a standard by cell size reject logic 221, which rejects the measurement if the cell is too small. The cell size representation is also output to a queue.

When the threshold established by the cell boundary reference line 216 is exceeded by the magnitude of the incoming slit-scan contour, the threshold being set at a level experimentally determined to be indicative of the beginning of cell passage through the excitation region, a suitable signal from the analog-to-digital conversion control 218 activates the analog-to-digital converter 208.

The output of the digital analog converter 208 is also connected to the input of a peak value register 218, which may comprise a plurality of D-type flip-flops. When the peak value register 218 is clocked by a PEAK DETECT signal on the line 212 from the hysteresis filter 204, the value on the D input is transferred to the Q output of the peak value register 218, and examined by peak height reject logic 220 which rejects the measurement if the contour peak height exceeds a predetermined threshold.

The PEAK DETECT line 212 from the hysteresis filter 204 also controls a peak address register 222 which receives an ADC ADDRESS input from the analog-to-digital conversion control 218, and outputs information concerning where in the queue peak height is stored.

The PEAK DETECT line 212 is also connected to a peak count detector 224, which serves to output a reject signal if an observed slit-scan contour has more than one peak, indicative of a binucleate cell or of overlapping cells.

Figure 21:
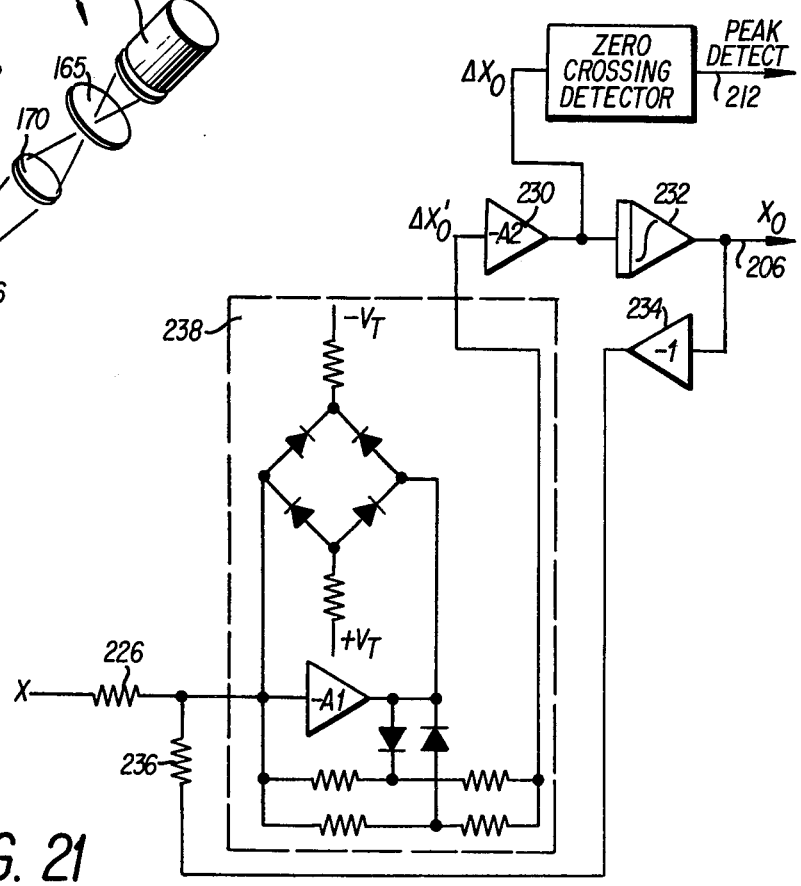
FIG. 21 is a block diagram depicting a hysteresis filter suitable for use in the contour pre-processor of FIG. 20.

FIG. 21 is an electrical schematic diagram of a hysteresis filter, suitable for use as the non-linear hysteresis filter 204 of the FIG. 20 pre-processor. In FIG. 21, an incoming signal (X) is coupled through an input resistor 226 to a dead-space limiter 228 which generates an output $\Delta X'_0$ proportional to $(X-X_0)$ only if the magnitude of $(X-X_0)$ is greater than the threshold value $V_T$.

This $X'_0$ output is amplified by an amplifier 230 to generate a difference signal $\Delta X_0$. $\Delta X_0$ is supplied to an integrator 232 which generates an output $X_0$, which is inverted by an inverter 234 and fed back to the input through a feedback resistor 236.

In operation, when a small change in the incoming signal X occurs, it produces a change in the output $X_0$ only if the incoming change is large enough to make the absolute value of $(X-X_0)$ greater than $V_T$. $V_0$ is thus a filtered version of X in which small bumps or dips in X do not appear in $X_0$ unless the height or depth respectively are greater than $V_T$.

Generation of the PEAK DETECT signal utilizes $\Delta X_0$ which appears at the output of the amplifier 230. $\Delta X_0$ is in fact the derivative of $X_0$, since it is integrated by the integrator 232 to generate $X_0$. Any time $\Delta X_0$ changes from positive to negative, a local peak occurs in $X_0$. These changes in $\Delta X_0$ are converted to logic level transitions by a zero crossing detector 238, the output of which drives the PEAK DETECT line 212. A transition from logic high to logic low at the output of the zero crossing detector 238 signifies a peak in $X_0$.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A flow cytofluorometer for obtaining multidimensional slit-scan type fluorescence contours of a biological cell, comprising:

means for conveying the cell along a flow axis;

means for providing a substantially planar beam of electromagnetic radiation for exciting secondary fluorescence in the cell, the flow axis intersecting but not lying within the plane of the beam such that the cell passes through the beam and a plurality of first substantially planar parallel cross-sections of the cell are successively excited to secondary fluorescence;

means for measuring secondary fluorescence from the first cellular cross-sections as the cell passes through the beam so as to generate a slit-scan type contour along a first axis perpendicular to the first cellular cross-sections; and means for measuring secondary fluorescence from each of a first plurality of substantially linear portions of the cell as the cell passes through the beam, the linear portions of the first plurality being defined by the intersections of each of a plurality of second substantially planar parallel cross-sections of the cell with each of the first cross-sections, the cell second cross-sections being parallel to the flow axis, and for generating first integrations for each individual second cross-section of the measured secondary fluorescences of all the linear portions therein, such that the resultant first integrations collectively represent a slit-scan type contour along a second axis perpendicular to the second cross-sections.

2. A flow cytofluorometer according to claim 1, further comprising:

means for measuring secondary fluorescence from each of a second plurality of substantially linear portions of the cell as the cell passes through the beam, the linear portions of the second plurality being defined by intersections of each of a plurality of third substantially planar parallel cross-sections of the cell with each of the first cellular cross-sections, the cell third cellular cross-sections being parallel to the flow axis and not parallel to the second cellular cross-sections, and for generating second integrations for each individual third cellular cross-section of the measured secondary fluorescences of all the linear portions therein, such that the resultant second integrations collectively represent a slit-scan type contour along a third axis perpendicular to the third cellular cross-sections.

3. A flow cytofluorometer according to claim 2, wherein the plane of the beam of electromagnetic radiation is perpendicular to the flow axis.

4. A flow cytofluorometer according to claim 3, wherein the second and third planar portions are perpendicular to each other.

5. A flow cytofluorometer according to claim 4, wherein in a Cartesian coordinate system:

the first cellular axis and the flow axis coincide and may be termed the Z-axis;

the second cellular axis perpendicular to the second cellular cross-sections may be termed the X-axis; and the third cellular axis perpendicular to the third cellular cross-sections may be termed the Y-axis.

6. A flow cytofluorometer according to claim 1, wherein the second cellular cross-sections are contiguous.

7. A flow cytofluorometer according to claim 2, wherein the second cellular cell cross-sections are contiguous and the third cellular cross-sections are contiguous.

8. A flow cytofluorometer according to claim 1, wherein said means for measuring secondary fluorescence from each of a first plurality of substantially linear portions and for generating first integrations collectively representing a slit-scan type contour along a second cellular axis comprises:

a first linear array of photodetector elements responsive to secondary fluorescence;

first means for imaging the linear portions of the first plurality onto said first linear array as each of the first cellular cross-sections passes through the beam and is excited to fluorescence, said first imaging means producing end-on imaging of individual linear portions of the first plurality which lie in each of the first cellular cross-sections; and means for integrating with respect to time the secondary fluorescences of the linear portions imaged on each photodetector element.

9. A flow cytofluorometer according to claim 8, wherein each photodetector element itself is time-integrating and accordingly includes said means for integrating with respect to time.

10. A flow cytofluorometer according to claim 8, wherein the plane of the beam is perpendicular to the flow axis, and said first imaging means views the linear portions of the first plurality along a first optical axis perpendicular to the flow axis.

11. A flow cytofluorometer according to claim 1, wherein said means for measuring secondary fluorescence from each of a first plurality of substantially linear portions and for generating first integrations collectively representing a slit scan type contour along a second cellular axis comprises:

a first linear array of time integrating photodetector elements responsive to secondary fluorescence; and first means for imaging the linear portions of the first plurality onto said first linear array as each of the first cell cross-sections passes through the beam and is excited to fluorescence, said first imaging means producing end-on imaging of individual linear portions of the first plurality which lie in each of the first cellular cross-sections such that each photodetector element effectively integrates the secondary fluorescences of the linear portions imaged thereon.

12. Apparatus according to claim 11, wherein the plane of the beam is perpendicular to the flow axis, and said first imaging means views the linear portions of the first plurality along a first optical axis perpendicular to the flow axis.

13. A flow cytofluorometer according to claim 2, wherein said means for measuring secondary fluorescence from each of a first plurality of substantially linear portions and for generating first integrations collectively representing a slit scan type contour along a second cellular axis comprises:

a first linear array of photodetector elements responsive to secondary fluorescence, first means for imaging the linear portions of the first plurality onto said first linear array as each of the first cellular cross-sections passes through the beam and is excited to fluorescence, said first imaging means producing end-on imaging of individual linear portions of the first plurality which lie in each of the first cellular cross-sections, and means for integrating with respect to time the secondary fluorescences of the linear portions imaged on each photodetector element of said first linear array; and wherein said means for measuring secondary fluorescence from each of a second plurality of substantially linear portions and for generating second integrations collectively representing a slit scan type contour along a third cellular axis comprises:

a second linear array of photodetector elements responsive to secondary fluorescence, and second means for imaging the linear portions of the second plurality onto said second linear array as each of the first cellular cross-sections passes through the beam and is excited to fluorescence, said second imaging means producing end-on imaging of individual linear portions of the second plurality which lie in each of the first cellular cross-sections, and means for integrating with respect to time the secondary fluorescences of the linear portions imaged on each photodetector element of said second linear array.

14. A flow cytofluorometer according to claim 13, wherein the plane of the beam is perpendicular to the flow axis, and said first and second imaging means respectively view the linear portions of the first plurality and the linear portions of the second plurality along respective first and second optical axes perpendicular to the flow axis and non-parallel to each other.

15. A flow cytofluorometer according to claim 2, wherein said means for measuring secondary fluorescence from each of a first plurality of substantially linear portions and for generating first integrations collectively representing a slit scan type contour along a second cellular axis comprises:

a first linear array of time integrating photodetector elements responsive to secondary fluorescence, and first means for imaging the linear portions of the first plurality onto said first linear array as each of the first cellular cross-sections passes through the beam and is excited to fluorescence, said first imaging means producing end-on imaging of individual linear portions of the first plurality which lie in each of the first cellular cross-sections such that each photodetector element effectively integrates the secondary fluorescences of the linear portions imaged thereon; and wherein said means for measuring secondary fluorescence from each of a second plurality of substantially linear portions and for generating second integrations collectively representing a slit scan type contour along a third cellular axis comprises:

a second linear array of time integrating photodetector elements responsive to secondary fluorescence, and second means for imaging the linear portions of the second plurality onto said second linear array as each of the first cellular cross-sections passes through the beam and is excited to fluorescence, said second imaging means producing end-on imaging of individual linear portions of the second plurality which lie in each of the first cellular cross-sections such that each photodetector element effectively integrates the secondary fluorescences of the linear portions imaged thereon.

16. A flow cytofluorometer according to claim 15, wherein the plane of the beam is perpendicular to the flow axis, and said first and second imaging means respectively view the linear portions of the first plurality and the linear portions of the second plurality along respective first and second optical axes perpendicular to the flow axis and non-parallel to each other.

17. A flow cytofluorometer according to claim 1, wherein said means for measuring secondary fluorescence from each of a first plurality of substantially linear portions and for generating first integrations collectively representing a slit-scan type contour along a second cellular axis comprises:

a first linear array of parallel elongated photodetector elements responsive to secondary fluorescence;

first means for imaging the linear portions of the first plurality onto said first linear array of elongated photodetector elements as each of the first cellular cross-sections passes through the beam and is excited to fluorescence, said first imaging means producing side imaging of individual linear portions of the first plurality which lie in each of the first cellular cross-sections onto corresponding photodetector elements; and means for integrating with respect to time the secondary fluorescences of the linear portions imaged on each photodetector element.

18. A flow cytofluorometer according to claim 17, wherein said first imaging means views the linear portions of the first plurality along an optical axis perpendicular to the plane of the beam of electromagnetic radiation.

19. A flow cytofluorometer according to claim 18, wherein the plane of the beam of electromagnetic radiation is perpendicular to the flow axis, and said optical axis of said first imaging means is coincident with the flow axis.

20. A flow cytofluorometer according to claim 19, wherein said first imaging means comprises a lens having an aperture along the optical and flow axis, through which aperture the cell passes.

21. A flow cytofluorometer according to claim 19, wherein said first imaging means comprises a mirror having an aperture along the optical and flow axis, through which aperture the cell passes.

22. A flow cytofluorometer according to claim 2, wherein said means for measuring secondary fluorescence from each of a first plurality of substantially linear portions and for generating first integrations collectively representing a slit scan type contour along a second cellular axis comprises:

a first linear array of parallel elongated photodetector elements responsive to secondary fluorescence, first means for imaging the linear portions of the first plurality onto said first linear array of elongated photodetector elements as each of the first cell cross-sections passes through the beam and is excited to fluorescence, said first imaging means producing side imaging of individual linear portions of the first plurality which lie in each of the first cellular cross-sections onto corresponding photodetector elements, and means for integrating with respect to time the secondary fluorescences of the linear portions imaged on each photodetector element of said first linear array; and wherein said means for measuring secondary fluorescence from each of a second plurality of substantially linear portions and for generating second integrations collectively representing a slit-scan type contour along a third cellular axis comprises:

a second linear array of parallel elongated photodetector elements responsive to secondary fluorescence, second means for imaging the linear portions of the second plurality onto said second linear array of elongated photodetector elements as each of the first cell cross-sections passes through the beam and is excited to fluorescence, said second imaging means producing side imaging of individual linear portions of the second plurality which lie in each of the first cellular cross-sections onto corresponding photodetector elements, and means for integrating with respect to time the secondary fluorescences of the linear portions imaged on each photodetector element of said second linear array.

23. A flow cytofluorometer according to claim 22, wherein said first and second imaging means respectively view the linear portions of the first plurality and the linear portions of the second plurality along an optical axis perpendicular to the plane of the beam of electromagnetic radiation.

24. A flow cytofluorometer according to claim 23, wherein the plane of the beam of electromagnetic radiation is perpendicular to the flow axis, and said first and second imaging means share a common optical axis coincident with the flow axis.

25. A flow cytofluorometer according to claim 24, wherein said first and second imaging means comprise a shared lens having an aperture along the optical and flow axis, through which aperture the cell passes.

26. A flow cytofluorometer according to claim 24, wherein said first and second imaging means comprise a shared mirror having an aperture along the optical and flow axis, through which aperture the cell passes.

27. A flow cytofluorometer according to claim 1, wherein said means for measuring secondary fluorescence from each of a first plurality of substantially linear portions and for generating first integrations collectively representing a slit-scan type contour along a second cellular axis comprises:

a first linear array of parallel elongated time integrating photodetector elements responsive to secondary fluorescence; and first means for imaging the linear portions of the first plurality onto said first linear array of elongated photodetector elements as each of the first cell cross-sections passes through the beam and is excited to fluorescence, said first imaging means producing side imaging of individual linear portions of the first plurality which lie in each of the first cellular cross-sections such that each photodetector element effectively integrates the fluorescence of the linear portions imaged thereon.

28. A flow cytofluorometer according to claim 27, wherein said first imaging means views the linear portions of the first plurality along an optical axis perpendicular to the plane of the beam of electromagnetic radiation.

29. A flow cytofluorometer according to claim 28, wherein the plane of the beam of electromagnetic radiation is perpendicular to the flow axis, and said optical axis of said first imaging means is coincident with the flow axis.

30. A flow cytofluorometer according to claim 29, wherein said first imaging means comprises a lens having an aperture along the optical and flow axis, through which aperture the cell passes.

31. A flow cytofluorometer according to claim 29, wherein said first imaging means comprises a mirror having an aperture along the optical and flow axis, through which aperture the cell passes.

32. A flow cytofluorometer according to claim 2, wherein said means for measuring secondary fluorescence from each of a first plurality of substantially linear portions and for generating first integrations collectively representing a slit scan type contour along a second cellular axis comprises:
a first linear array of parallel elongated time integrating photodetector elements responsive to secondary fluorescence, and
first means for imaging the linear portions of the first plurality onto said first linear array of elongated photodetector elements as each of the first cell cross-sections passes through the beam and is excited to fluorescence, said first imaging means producing side imaging of individual linear portions of the first plurality which lie in each of the first cell cross-sections such that each photodetector element effectively integrates the fluorescences of the linear portions imaged thereon; and
wherein said means for measuring secondary fluorescence from each of a second plurality of substantially linear portions and for generating second integrations collectively representing a slit scan type contour along a third cellular axis comprises:
a second linear array of parallel elongated time integrating photodetector elements responsive to secondary fluorescence, and
second means for imaging the linear portions of the second plurality onto said second linear array of elongated photodetector elements as each of the first cell cross-sections passes through the beam and is excited to fluorescence, said second imaging means producing side imaging of individual linear portions of the second plurality which lie in each of the first cell cross-sections such that each photodetector element effectively integrates the fluorescences of the linear portions imaged thereon.

33. A flow cytofluorometer according to claim 32, wherein said first and second imaging means respectively view the linear portions of the first plurality and the linear portions of the second plurality along an optical axis perpendicular to the plane of the beam of electromagnetic radiation.

34. A flow cytofluorometer according to claim 33, wherein the plane of the beam of electromagnetic radiation is perpendicular to the flow axis, and said first and second imaging means share a common optical axis coincident with the flow axis.

35. A flow cytofluorometer according to claim 34, wherein said first and second imaging means comprise a shared lens having an aperture along the optical and flow axis, through which aperture the cell passes.

36. A flow cytofluorometer according to claim 34, wherein said first and second imaging means comprise a shared mirror having an aperture along the optical and flow axis, through which aperture the cell passes.

37. A flow cytofluorometer comprising:
means for conveying a cell along a flow axis;
means for providing a substantially planar beam of electromagnetic radiation for exciting secondary fluorescence in the cell, the flow axis intersecting but not lying within the plane of the beam such that the cell passes through the beam and a plurality of first substantially planar parallel cross-sections of the cell are successively excited to secondary fluorescence;
means for measuring secondary fluorescence from the first cellular cross-sections as the cell passes through the beam so as to generate a slit-scan type contour along a first axis perpendicular to the first cellular cross-sections;
a two-dimensional array of photodetector elements responsive to secondary fluorescence; and
means for imaging the first cellular cross-sections onto said two-dimensional array as each of the first cellular cross-sections passes through the beam and is excited to fluorescence, said imaging means viewing the first cellular cross-sections along an optical axis perpendicular to the plane of the beam of electromagnetic radiation.

38. A flow cytofluorometer according to claim 37, wherein the plane of the beam of electromagnetic radiation is perpendicular to the flow axis, and said optical axis of said imaging means is coincident with the flow axis.

39. A flow cytofluorometer according to claim 38, wherein said imaging means comprises a lens having an aperture along the optical and flow axis, through which aperture the cell passes.

40. A flow cytofluorometer according to claim 38, wherein said imaging means comprises a mirror having an aperture along the optical and flow axis, through which aperture cell passes.

41. A flow cytofluorometer comprising:
means for conveying a cell along a flow axis;
means for providing a substantially planar beam of electromagnetic radiation for exciting secondary fluorescence in the cell, the flow axis intersecting but not lying within the plane of the beam such that the cell passes through the beam and a plurality of first substantially planar parallel cross-sections of the cell are successively excited to secondary fluorescence;
means for measuring secondary fluorescence from the first cellular cross-sections as the cell passes through the beam so as to generate a slit-scan type contour along a first axis perpendicular to the first cellular cross-sections;
a two-dimensional array of photodetector elements responsive to secondary fluorescence;
means for imaging the first cellular cross-sections onto said two-dimensional array as each of the first cellular cross-sections passes through the beam and is excited to fluorescence, said imaging means viewing the first cellular cross-sections along an optical axis perpendicular to the plane of the beam
of electromagnetic radiation; and means for integrating with respect to time the fluorescence imaged on each element of said two-dimensional array.

42. A flow cytofluorometer comprising:

means for conveying a cell along a flow axis;

means for providing a substantially planar beam of electromagnetic radiation for exciting secondary fluorescence in the cell, the flow axis intersecting but not lying within the plane of the beam such that the cell passes through the beam and a plurality of first substantially planar parallel cross-sections of the cell are successively excited to secondary fluorescence;

means for measuring secondary fluorescence from the first cellular cross-sections as the cell passes through the beam so as to generate a slit-scan type controur along a first axis perpendicular to the first cellular cross-sections;

a two-dimensional array of time-integrating photodetector elements responsive to secondary fluorescence; and means for imaging the first cellular cross-sections onto said two-dimensional array as each of the first cellular cross-sections passes through the beam and is excited to fluorescence, said imaging means viewing the first cellular cross-sections along an optical axis perpendicular to the plane of the beam of electromagnetic radiation.

43. A flow cytofluorometer according to claim 41, which further comprises means for generating separate integrations by rows and columns of the time-integrated fluorescences imaged on each photodetector element such that the resultant integrations represent slit-scan type contours along two perpendicular axes each perpendicular to the optical axis.

44. A flow cytofluorometer according to claim 42, which further comprises means for generating separate integrations by rows and columns of the secondary fluorescences accumulated by the elements of said array such that the resultant integrations represent slit-scan type contours along two cellular axes each perpendicular to the optical axis.

45. A flow cytofluorometer for obtaining multidimensional slit-scan type fluorescence contours of a biological cell, comprising:

means for conveying the cell along a flow axis;

means for providing a substantially planar beam of electromagnetic radiation for exciting secondary fluorescence in the cell, the flow axis intersecting but not lying within the plane of the beam such that the cell passes through the beam and a plurality of first substantially planar parallel cross-sections of the cell are successively excited to secondary fluorescence;

means for measuring secondary fluorescence from the first cellular cross-sections as the cell passes through the beam so as to generate a slit-scan type contour along a first cellular axis perpendicular to the first cellular cross-sections;

a first linear array of time integrating photodetector elements responsive to secondary fluorescence; and first means for imaging each of a first plurality of substantially linear portions of the cell onto said first linear array as each of the first cellular cross-sections passes through the beam and is excited to fluorescence, the linear portions of the first plurality being defined by the intersections of each of a plurality of second substantially planar parallel cross-sections of the cell with each of the first cellular cross-sections, the second cellular cross-sections being parallel to the flow axis, said first imaging means producing end-on imaging of individual linear portions of the first plurality which lie in each of the first cellular cross-sections such that each photodetector element integrates the secondary fluorescences of the linear portions imaged thereon;

whereby the resultant integrations in said photodetector elements of said first linear array collectively represent a slit-scan type contour along a second cellular axis perpendicular to the second cellular cross-sections.

46. A flow cytofluorometer according to claim 45, further comprising:

a second linear array of time integrating photodetector elements responsive to secondary fluorescence; and second means for imaging each of a first plurality of substantially linear portions of the cell onto said second linear array as each of the first cellular cross-sections passes through the beam and is excited to fluorescence, the linear portions of the second plurality being defined by the intersections of each of a plurality of third substantially planar parallel cross-sections of the cell with each of the first cellular cross-sections, the third cellular cross-sections being parallel to the flow axis and not parallel to the second cellular cross-sections, said second imaging means producing end-on imaging of individual linear portions of the second plurality which lie in each of the first cellular cross-sections such that each photodetector element integrates the secondary fluorescences of the linear portions imaged thereon;

whereby the resultant integrations in said photodetector elements of said second linear array collectively represent a slit scan type contour along a third cellular axis perpendicular to the third cellular cross-sections.

47. A flow cytofluorometer for obtaining multidimensional slit-scan type fluorescence contours of a biological cell, comprising:

means for conveying the cell along a flow axis;

means for providing a substantially planar beam of electromagnetic radiation for exciting secondary fluorescence in the cell, the flow axis intersecting but not lying within the plane of the beam such that the cell passes through the beam and a plurality of first substantially planar parallel cross-sections of the cell are successively excited to secondary fluorescence;

means for measuring secondary fluorescence from the first cellular cross-sections as the cell passes through the beam so as to generate a slit-scan type contour along a first cellular axis perpendicular to the firt cellular cross-sections;

a first linear array of parallel elongated time integrating photodetector elements responsive to secondary fluorescence; and first means for imaging each of a first plurality of substantially linear portions of the cell onto said first linear array as each of the first cellular cross-sections passes through the beam and is excited to fluorescence, the linear portions of the first plurality being defined by the intersections of each of a plurality of second substantially planar parallel cross-sections of the cell with each of the first cellular cross-sections, the second cellular cross-sections being parallel to the flow axis, said first imaging means producing side imaging of individual linear portions of the first plurality which lie in each of the first cellular cross-sections such that each photodetector element effectively integrates the fluorescence of the linear portions imaged thereon;

whereby the resultant integrations in said photodetector elements of said first linear array collectively represent a slit-scan type contour along a second cellular axis perpendicular to the second cellular cross-sections.

48. A flow cytofluorometer according to claim 47, further comprising:
a second linear array of parallel elongated time integrating photodetector elements responsive to secondary fluorescence; and
second means for imaging each of a first plurality of substantially linear portions of the cell onto said second linear array as each of the first cellular cross-sections passes through the beam and is excited to fluorescence, the linear portions of the second plurality being defined by the intersections of each of a plurality of third substantially planar parallel cross-sections of the cell with each of the first cellular cross-sections, the third cellular cross-sections being parallel to the flow axis and not parallel to the second cellular cross-sections, said second imaging means producing side imaging of individual linear portions of the second plurality which lie in each of the first cell cross-sections onto corresponding photodetector elements;
whereby the resultant integrations in said photodetector elements of said second linear array collectively represent a slit-scan type contour along a third cellular axis perpendicular to the third cellular cross-sections.

49. A flow meter for obtaining multidimensional slit-scan type photometric contours of a particle, comprising:
means for conveying the particle along a flow axis;
means for providing a substantially planar beam of electromagnetic radiation for slit-scan type illumination of the particle, the flow axis intersecting but not lying within the plane of the beam such that the particle passes through the beam and a plurality of first substantially planar parallel cross-sections of the particle are successively illuminated;
means for measuring radiation resulting from interaction of each of the first particle cross-sections with the beam as the particle passes through the beam so as to generate a slit-scan type photometric contour along a first axis perpendicular to the first particle cross-sections; and
means for measuring radiation resulting from interaction with the beam of each of a first plurality of substantially linear portions of the particle as the particle passes through the beam, the linear portions of the first plurality being defined by the intersections of each of a plurality of second substantially planar parallel cross-sections of the particle with each of the first cross-sections, the particle second cross-sections being parallel to the flow axis, and for generating first integrations for each individual second cross-section of the measured radiation resulting from all the linear portions therein, such that the resultant first integrations collectively represent a slit-scan type photometric contour along a second axis perpendicular to the second particle cross-sections.

50. A flow meter according to claim 49, wherein said means for measuring radiation resulting from interaction with the beam of each of a first plurality of substantially linear portions and for generating first integrations collectively representing a slit-scan type photometric contour along a second particle axis comprises:
a first linear array of photodetector elements responsive to radiation resulting from particle interaction with the beam;
first means for imaging the linear portions of the first plurality onto said first linear array as each of the first particle cross-sections passes through and interacts with the beam, said first imaging means producing end-on imaging of individual linear portions of the first plurality which lie in each of the first particle cross-sections; and
means for integrating with respect to time the resultant radiation for each of the linear portions imaged on each photodetector element.

51. A flow meter according to claim 49, wherein said means for measuring radiation resulting from interaction with the beam of each of a first plurality of substantially linear portions and for generating first integrations collectively representing a slit-scan type photometric contour along a second particle axis comprises:
a first linear array of parallel elongated photodetector elements responsive to radiation resulting from particle interaction with the beam;
first means for imaging the linear portions of the first plurality onto said first linear array of elongated photodetector elements as each of the first particle cross-sections passes through and interacts with the beam, said first imaging means producing side imaging of individual linear portions of the first plurality which lie in each of the first particle cross-sections onto corresponding photodetector elements; and
means for integrating with respect to time the resultant radiations for each of the linear portions imaged on each photodetector element.

52. A flow meter according to claim 49, further comprising:
means for measuring radiation resulting from interaction with the beam of each of a second plurality of substantially linear portions of the particle as the particle passes through the beam, the linear portions of the second plurality being defined by intersections of each of a plurality of third substantially planar parallel cross-sections of the particle with each of the first cellular cross-sections, the third particle cross-sections being parallel to the flow axis and not parallel to the second particle cross-sections, and for generating second integrations for each individual third particle cross-section of the measured secondary fluorescences of all the linear portions therein, such that the resultant second integrations collectively represent a slit-scan type photometric contour along a third particle axis perpendicular to the third particle cross-sections.

53. A flow meter according to claim 52, wherein said means for measuring radiation resulting from interaction with the beam of each of a first plurality of substantially linear portions and for generating first integrations collectively representing a slit-scan type photometric contour along a second particle axis comprises:

a first linear array of photodetector elements responsive to radiation resulting from particle interaction with the beam, first means for imaging the linear portions of the first plurality onto said first linear array as each of the first particle cross-sections passes through and interacts with the beam, said first imaging means producing end-on imaging of individual linear portions of the first plurality which lie in each of the first particle cross-sections, and means for integrating with respect to time the resultant radiation for each of the linear portions imaged on each photodetector element of said first linear array; and wherein said means for measuring radiation resulting from interaction with the beam of each of a second plurality of substantially linear portions and for generating second integrations collectively representing a slit-scan type photometric contour along a third particle axis comprises:

a second linear array of time integrating photodetector elements responsive to radiation resulting from particle interaction with the beam, and second means for imaging the linear portions of the second plurality onto said second linear array as each of the first particle cross-sections passes through and interacts with the beam, said second imaging means producing end-on imaging of individual linear portions of the second plurality which lie in each of the first particle cross-sections, and means for integrating with respect to time the resultant radiation for each of the linear portions imaged on each photodetector element of said second linear array.

54. A flow meter according to claim 52, wherein said means for measuring radiation resulting from interaction with the beam of each of a first plurality of substantially linear portions and for generating first integrations collectively representing a slit-scan type photometric contour along a second particle axis comprises:

a first linear array of parallel elongated photodetector elements responsive to radiation resulting from particle interaction with the beam, first means for imaging the linear portions of the first plurality onto said first linear array of elongated photodetector elements as each of the first cellular cross-sections passes through and interacts with the beam, said first imaging means producing side imaging of individual linear portions of the first plurality which lie in each of the first particle cross-sections onto corresponding photodetector elements, and means for integrating with respect to time the resultant radiation for each of the linear portions imaged on each photodetector element of said first linear array; and wherein said means for measuring radiation resulting from interaction with the beam of each of a second plurality of substantially linear portions and for generating second integrations collectively representing a slit-scan type photometric contour along a third particle axis comprises:

a second linear array of parallel elongated photodetector elements responsive to radiation resulting from particle interaction with the beam, second means for imaging the linear portions of the second plurality onto said second linear array of elongated photodetector elements as each of the first particle cross-sections passes through and interacts with the beam, said second imaging means producing side imaging of individual linear portions of the second plurality which lie in each of the first particle cross-sections onto corresponding photodetector elements, and means for integrating with respect to time the resultant radiation for each of the linear portions imaged on each photodetector element of said second linear array.

55. A flow cytofluorometer for obtaining multidimensional slit-scan type fluorescence contours of a biological cell, comprising:

means for conveying the cell along a flow axis;

means for providing a beam of electromagnetic radiation for exciting secondary fluorescence in the cell, the beam focus being such that a central region along the flow axis is illuminated and a volume of the cell is excited to fluorescence as the cell passes through the illuminated region;

a plurality of imaging systems for slit imaging across the central region, the planes of the resultant slit-imaged portions in the central region being non-parallel with each other and non-parallel with said flow axis; and photodetector means coupled to each of said imaging systems for responding to fluorescence from each of the slit-imaged portions in the central region, each of said photodetector means outputting a slit-scan type contour along a cellular axis perpendicular to the plane of the respective slit-imaged portion.

56. A flow cytofluorometer according to claim 55, which comprises three slit-imaging systems defining three mutually orthogonal planar slit-imaged portions in the central region.

57. A flow fluorometer for obtaining multi-dimensional slit-scan type fluorescence contours of a particle, comprising:

means for conveying the particle along a flow axis;

means for providing a substantially planar beam of electromagnetic radiation for exciting secondary fluorescence in the particle, the flow axis intersecting but not lying within the plane of the beam such that the particle passes through the beam and a plurality of first substantially planar parallel cross-sections of the particle are successively excited to secondary fluorescence;

means for measuring secondary fluorescence from the first particle cross-sections as the particle passes though the beam so as to generate a slit-scan type contour along a first axis perpendicular to the first particle cross-sections; and means for measuring secondary fluorescence from each of the first plurality of substantially linear portions of the particle as the particle passes through the beam, the linear portions of the first plurality being defined by the intersections of each of a plurality of second substantially planar parallel cross-sections of the particle with each of the first cross-sections, the particle second cross-sections being parallel to the flow axis, and for generating first integrations for each individual second cross-section of the measured secondary fluorescences of all the linear portions therein, such that the resultant first integrations collectively represent a slit-scan type contour along a second axis perpendicular to the second cross-sections.

58. A flow fluorometer according to claim 57, further comprising:
means for measuring secondary fluorescence from each of a second plurality of substantially linear portions of the particle as the particle passes through the beam, the linear portions of the second plurality being defined by intersections of each of a plurality of third substantially planar parallel cross-sections of the particle with each of the first particle cross-sections, the particle third cellular cross-sections being parallel to the flow axis and not parallel to the second particle cross-sections, and for generating second integrations for each individual third particle cross-section of the measured secondary fluorescences of all the linear portions therein, such that the resultant second integrations collectively represent a slit-scan type contour along a third axis perpendicular to the third particle cross-sections.

59. A flow fluorometer according to claim 57, wherein said means for measuring secondary fluorescence from each of a first plurality of substantially linear portions and for generating first integrations collectively representing a slit scan type contour along a second axis comprises:
a first linear array of time integrating photodetector elements responsive to secondary fluorescence; and
first means for imaging the linear portions of the first plurality onto said first linear array as each of the first cross-sections passes through the beam and is excited to fluorescence, said first imaging means producing end-on imaging of individual linear portions of the first plurality which lie in each of the first cross-sections such that each photodetector element effectively integrates the secondary fluorescences of the linear portions imaged thereon.

60. A flow fluorometer according to claim 58, wherein said means for measuring secondary fluorescence from each of a first plurality of substantially linear portions and for generating first integrations collectively representing a slit-scan type contour along a second axis comprises:
a first linear array of photodetector elements responsive to secondary fluorescence,
first means for imaging the linear portions of the first plurality onto said first linear array as each of the first cross-sections passes through the beam and is excited to fluorescence, said first imaging means producing end-on imaging of individual linear portions of the first plurality which lie in each of the first cross-sections, and
means for integrating with respect to time the secondary fluorescences of the linear portions imaged on each photodetector element of said first linear array; and
wherein said means for measuring secondary fluorescence from each of a second plurality of substantially linear portions and for generating second integrations collectively representing a slit-scan type contour along a third axis comprises:
a second linear array of photodetector elements responsive to secondary fluorescence,
second means for imaging the linear portions of the second plurality onto said second linear array as each of the first cross-sections passes through the beam and is excited to fluorescence, said second imaging means producing end-on imaging of individual linear portions of the second plurality which lie in each of the first cross-sections, and
means for integrating with respect to time the secondary fluorescences of the linear portions imaged on each photodetector element of said second linear array.

61. A flow fluorometer according to claim 57, wherein said means for measuring secondary fluorescence from each of a first plurality of substantially linear portions and for generating first integrations collectively representing a slit-scan type contour along a second axis comprises:
a first linear array of parallel elongated photodetector elements responsive to secondary fluorescence;
first means for imaging the linear portions of the first plurality onto said first linear array of elongaged photodetector elements as each of the first cross-sections passes through the beam and is excited to fluorescence, said first imaging means producing side imaging of individual linear portions of the first plurality which lie in each of the first cross-sections onto corresponding photodetector elements; and
means for integrating with respect to time the secondary fluorescences of the linear portions imaged on each photodetector element.

62. A flow fluorometer according to claim 58, wherein said means for measuring secondary fluorescence from each of a first plurality of substantially linear portions and for generating first integrations collectively representing a slit-scan type contour along a second axis comprises:
a first linear array of parallel elongated photodetector elements responsive to secondary fluorescence,
first means for imaging the linear portions of the first plurality onto said first linear array of elongated photodetector elements as each of the first cross-sections passes through the beam and is excited to fluorescence, said first imaging means producing side imaging of individual linear portions of the first plurality which lie in each of the first cross-sections onto corresponding photodetector elements, and
means for integrating with respect to time the secondary fluorescences of the linear portions imaged on each photodetector element of said first linear array; and
wherein said means for measuring secondary fluorescence from each of a second plurality of substantially linear portions and for generating second integrations collectively representing a slit-scan type contour along a third axis comprises:
a second linear array of parallel elongated photodetector elements responsive to secondary fluorescence,
second means for imaging the linear portions of the second plurality onto said second linear array of elongated photodetector elements as each of the first cross-sections passes through the beam and is excited to fluorescence, said second imaging means producing side imaging of individual linear portions of the second plurality which lie in each of the first cross-sections onto corresponding photodetector elements, and means for integrating with respect to time the secondary fluorescences of the linear portions imaged on each photodetector element of said second linear array.

63. A flow fluorometer comprising:

means for conveying a particle along a flow axis;

means for providing a substantially planar beam of electromagnetic radiation for exciting secondary fluorescence in the particle, the flow axis intersecting but not lying within the plane of the beam such that the particle passes through the beam and a plurality of first substantially planar parallel cross-sections of the particle are successively excited to secondary fluorescence;

means for measuring secondary fluorescence from the first particle cross-sections as the particle passes through the beam so as to generate a slit-scan type contour along a first axis perpendicular to the first particle cross-sections;

a two-dimensional array of photodetector elements responsive to secondary fluorescence; and means for imaging the first particle cross-sections onto said two-dimensional array as each of the first cross-sections passes through the beam and is excited to fluorescence, said imaging means viewing the first cross-sections along an optical axis perpendicular to the plane of the beam of electromagnetic radiation.

* * * * *